(12) United States Patent
Ukita et al.

(10) Patent No.: US 6,214,996 B1
(45) Date of Patent: Apr. 10, 2001

(54) NAPHTHALENE DERIVATES, PROCESS FOR THE PREPARATION THEREOF, AND INTERMEDIATES THEREFOR

(75) Inventors: Tatsuzo Ukita, Kobe; Katsuo Ikezawa, Urawa; Shinsuke Yamagata, Mishima-gun, all of (JP)

(73) Assignee: Tanabe Seiyaku Co., Ltd., Osaka (JP)

( * ) Notice: Subject to any disclaimer, the term of this patent is extended or adjusted under 35 U.S.C. 154(b) by 0 days.

(21) Appl. No.: 09/201,820

(22) Filed: Dec. 1, 1998

Related U.S. Application Data

(62) Division of application No. 08/663,991, filed on Jun. 14, 1996.

(30) Foreign Application Priority Data

Jun. 15, 1995 (JP) .................................................. 7-149288

(51) Int. Cl.[7] ...................... C07D 295/00; C07D 401/00; C07D 403/00; C07D 215/00; A61K 31/44
(52) U.S. Cl. ........................... 546/237; 546/144; 546/14; 546/152; 546/156; 546/304; 546/141; 546/139; 544/106; 544/111; 544/358; 544/194; 544/359; 544/360; 544/361; 544/363; 544/180; 544/1; 514/352; 514/231.5; 514/311; 514/333; 514/334
(58) Field of Search .................................. 546/141, 144, 546/14, 155; 544/111, 149, 360, 363, 194, 180, 237, 354, 355, 315, 318, 124, 239, 238; 514/352, 231.5, 311

(56) References Cited

FOREIGN PATENT DOCUMENTS 0 557 016   8/1993  (EP) .
0 731 084   3/1995  (EP) .

OTHER PUBLICATIONS

Sakurai et al., "The Cyclization of Ethyl Acetoacetate and Ketones by Ammonium Acetate," Bull. Chem. Soc. Japan, 41:165–167 (1968).
Reinhoudt et al., "A Novel Route for the Synthesis of Benzo[b] Thiepins," Tetrahedron, 30:2431–2436 (1974).
Nicholson et al., "Differential Modulation of Tissue Function and Therapeutic Potential of Selective Inhibitors of Cyclic Nucleotide Phosphodiesterase Isoenzymes," Trends in Pharmacol., 12:19 (1991).

*Primary Examiner*—Sabiha N. Qazi
(74) *Attorney, Agent, or Firm*—Finnegan, Henderson, Farabow, Garrett & Dunner, L.L.P.

(57) ABSTRACT

Naphthalene derivatives of the formula [I]:

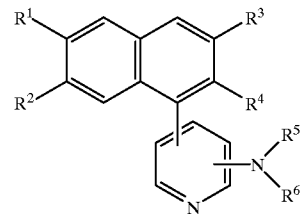

wherein $R^1$ and $R^2$ are the same or different and are each H, protected or unprotected OH, one of $R^3$ and $R^4$ is protected or unprotected hydroxymethyl, and the other is H, lower alkyl, or protected or unprotected hydroxymethyl, $R^5$ and $R^6$ are, the same or different and are each H, substituted or unsubstituted lower alkyl, substituted or unsubstituted phenyl or protected or unprotected $NH_2$, or both combine together with the adjacent N to form substituted or unsubstituted heterocyclic group, and pharmaceutically acceptable salts thereof, these compounds showing excellent bronchoconstriction inhibitory activity, and hence, being useful in the prophylaxis or treatment of asthma.

14 Claims, No Drawings

NAPHTHALENE DERIVATES, PROCESS FOR THE PREPARATION THEREOF, AND INTERMEDIATES THEREFOR

This application is a division of application Ser. No. 08/663,991, Jun. 14, 1996.

TECHNICAL FIELD

This invention relates to novel naphthalene derivatives having antiasthmatic activity and intermediates for the preparation of said compounds.

PRIOR ART

There is known 1-(5-methyl-2(1H)-pyridon-3-yl) naphthalene [cf. Bulletin of The Chemical Society of Japan, Vol. 41, pp. 165–167 (1968)], but any pharmacological activity or any utility of this compound has never been known. There are also known certain naphthalene derivatives such as 1-[N-(2-methoxyethyl)-2(1H)-pyridon-4-yl]-2, 3-bis(hydroxymethyl)-6,7-diethoxynaphthalene having antiasthmatic activity [cf. European Patent Publication EP-557016-A1 (=U.S. Pat. No. 5,342,941)]. However, EP-557016-A1 does not disclose 1-pyridylnaphthalene derivatives in which the pyridyl group on 1-position of the naphthalene ring is substituted by a substituted or unsubstituted amino group.

It is known that intracellular second messengers such as cAMP and cGMP are decomposed and inactivated by phosphodiesterase (abbreviated as "PDE"). Currently, at least 7 different PDE isozyme gene families are recognized and these PDEs are widely distributed in many cell types and tissues. A PDE inhibitor increases the concentration of cAMP and cGMP in tissue cells and exhibits various pharmacological activities, for example, relaxation of vascular smooth muscle and airway smooth muscle, and induction of positive inotropic action and chronotropic action in the heart. Moreover, the PDE inhibitor can control the central function owing to increase of cAMP in the central system, that is, it can exhibit an antidepressant activity and improves memory and learning functions. In addition, it shows inhibition of platelet aggregation and inhibition of activation of inflammatory cells, and further shows lipocatabolic action in fatty cells [cf. C. D. Nicholson et al., Trends in Pharmacol., Vol. 12, p. 19 (1991)].

Accordingly, the PDE inhibitory agent is useful for the treatment of various diseases, such as bronchial asthma, thrombosis, depression, central hypofunction after cerebrovascular obstruction, cerebrovascular dementia, Alzheimer's type dementia, various inflammations, obesity, heart failure, and the like.

On the other hand, various antiasthmatic agents have been known, but those known agents have some defects such as insufficiency in effects for inhibiting bronchoconstriction and further insufficient removal of side effects on the heart, and hence, it has been demanded to develop a new type of antiasthmatic agent.

Theophylline is known as one of the representative PDE inhibitory agents and has hitherto been used for the treatment of asthma. However, since the PDE inhibitory activity of this agent is non-specific, it shows cardiotonic and central activities in addition to the bronchial smooth muscle relaxation. Thus, careful attention has to be paid to this agent in view of such side effects. Accordingly, it has been desired to develop a new medicament which can selectively inhibit phosphodiesterase IV (PDE IV) which largely exists much more in bronchial smooth muscle and inflammatory cells.

BRIEF DESCRIPTION OF THE INVENTION

An object of the invention is to provide novel naphthalene derivatives which have excellent bronchoconstriction inhibitory activity and/or selective PDE IV inhibitory activity and hence are useful as an antiasthmatic agent. Another object of the invention is to provide a process for the preparation of the novel naphthalene derivatives. A further object of the invention is to provide intermediates for the preparation of the above naphthalene derivatives.

DETAILED DESCRIPTION OF THE INVENTION

The present invention provides novel naphthalene derivatives of the formula [I]:

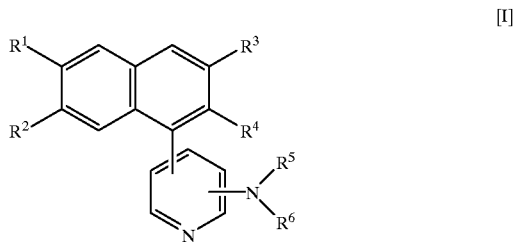

wherein $R^1$ and $R^2$ are the same or different and are each a hydrogen atom or a protected or unprotected hydroxy group; either one of $R^3$ and $R^4$ is a protected or unprotected hydroxy-substituted methyl group, and another is a hydrogen atom, a lower alkyl group, or a protected or unprotected hydroxy-substituted methyl group; $R^5$ and $R^6$ are the same or different and are each a hydrogen atom, a substituted or unsubstituted lower alkyl group, a substituted or unsubstituted phenyl group, or a protected or unprotected amino group, or both bond at their termini and combine with the adjacent nitrogen atom to form a substituted or unsubstituted heterocyclic group, and a pharmaceutically acceptable salt thereof.

The compounds [I] of this invention and salts thereof have potent bronchoconstriction inhibitory activity and are useful for the prophylaxis and treatment of asthma. The desired compounds [I] of this invention are characteristic in the excellent bronchoconstriction inhibitory activity with less side effects on the heart, for example, the compounds show more potent inhibitory activity to the bronchoconstriction induced by an antigen in comparison with theophylline.

The heterocyclic group formed by combining $R^5$ and $R^6$ together with the adjacent nitrogen atom includes monocyclic, bicyclic and tricyclic heterocyclic groups which may contain one or more additional heteroatoms selected from a nitrogen atom, an oxygen atom and a sulfur atom in addition to said adjacent nitrogen atom.

Suitable examples of the heterocyclic groups are pyridyl, quinolyl, isoquinolyl, cyclopenta[b]pyridyl, pyrro[2,3-b] pyridyl, imidazo[4,5-b]pyridyl, pyrido[2,3-d]thiazolyl, pyrido[2,3-d]oxazolyl, naphthyridinyl, quinoxalinyl, phtharazinyl, quinazolinyl, indolyl, pyridazinyl, azepinyl, azetidyl, isoindolyl, pyrrolyl, benzazepinyl, phenanthridinyl, benzothiadinyl, benzimidazolinyl, pyradinyl, morpholino, and the like. These heterocyclic groups may be partially or wholly hydrogenated.

The substituents for the lower alkyl group and phenyl group for $R^5$ and/or $R^6$ in the desired compounds [I] include a hydroxy group, mono- or di-hydroxy-lower alkyl group, and the like.

The protecting group of an amino group includes any conventional protecting groups for an amino group, for example, a lower alkanoyl group, and a phenyl-lower alkoxycarbonyl group.

In the desired compound [I] of this invention, wherein $R^1$ and/or $R^2$ is a protected hydroxy group, the protecting group for the hydroxy group may be any conventional pharmaceutically acceptable protecting group. For example, the protecting group in $R^1$ and/or $R^2$ is a substituted or unsubstituted lower alkanoyl group, a substituted or unsubstituted lower alkyl group and a substituted or unsubstituted cycloalkyl group. Preferred protecting group in $R^1$ and/or $R^2$ is an alkyl group, particularly a lower alkyl group.

In the desired compounds [I] of this invention, where $R^3$ and/or $R^4$ is a protected hydroxy group, the protecting group for the hydroxy group may be any conventional pharmaceutically acceptable protecting group. The protecting group are the groups which are hydrolyzed within the biobody and do not give any harmful by-product, for example, a substituted or unsubstituted lower alkanoyl group, a substituted or unsubstituted lower alkyl, lower alkoxycarbonyl or cycloalkyl group.

The substituted or unsubstituted lower alkanoyl group denotes lower alkanoyl groups which may optionally be substituted by 1 to 2 substituents selected from a protected or unprotected amino group, a carboxyl group, a lower alkoxycarbonyl group, a hydroxy group and a lower alkoxy group, and the substituted or unsubstituted alkyl group denotes alkyl groups which may optionally be substituted by a member selected from a lower alkoxycarbonyl group, a lower alkoxy group, an aryl group, and a lower alkyl-substituted piperazinylcarbonyl croup. The aryl group includes a phenyl croup, a lower alkoxy-substituted phenyl group, a naphthyl group.

The protecting group for the above protected amino group to be substituted onto the lower alkanoyl group may be any conventional protecting group for an amino group, for example, acyl groups such as a lower alkanoyl group (e.g. acetyl, propionyl), a lower alkoxycarbonyl group, or a phenyl-lower alkoxycarbonyl group (e.g. benzyloxycarbonyl).

The heterocyclic group may optionally be substituted by a member selected from (1) a lower alkenyl group, (2) a lower alkynyl group, (3) a lower alkylthio group, (4) a cycloalkyl group, (5) a trifluoromethyl group, (6) a cyano group, (7) a tetrazolyl group, (8) a formyl group, (9) an amino group, (10) a mono- or di-lower alkylamino group in which the lower alkyl moiety is optionally substituted by a morpholino group, a monocycloalkyl-substituted amino group, a pyridyl group, an imidazolyl group, a piperidyl group, or a pyrrolidinyl group, (11) a pyridyl group, (12) a morpholino group, (13) a lower alkyl-substituted triazolyl group, (14) a bis(hydroxy-lower alkyl)aminocarbonyl croup, (15) bis(tri-lower alkylsilyloxy-lower alkyl)aminocarbonyl group, (16) a morpholinocarbonyl group, (17) a lower alkyl-substituted piperazinylcarbonyl group, (18) a hydroxy-lower alkyl-substituted piperazinylcarbonyl group, (19) a tri-lower alkylsilyloxy-lower alkyl-substituted piperazinylcarbonyl group, (20) a lower alkoxycarbonyl group, (21) a carboxyl group, (22) a lower alkyl group being optionally substituted by a morpholino group or a pyridyl group, (23) a lower alkoxy croup being optionally substituted by a piperidyl group, a pyridyl group, a hydroxy group or a lower alkoxy group, (24) an oxo group, (25) a hydroxy group, (26) a pyrimidinyl group, (27) a phenyl group being optionally substituted by a di-lower alkylamino group or a halogen atom, (28) a halogen atom, (29) a nitro group, (30) an imidazolyl group, and (31) a lower alkylene-dioxy group. The heterocyclic group may be substituted by two or more of these substituents which may be the same or different.

Among the substituted heterocyclic groups, preferred one is a heterocyclic group which is substituted by at least one of an oxo group, a hydroxy group or an amino group, particularly a heterocyclic group having at least one oxo substituent, in view of the pharmacological activities. The heterocyclic group having at least one oxo substituent has preferably a partial structure of the formula:

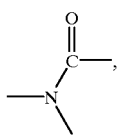

and suitable examples of these heterocyclic groups are as follows:

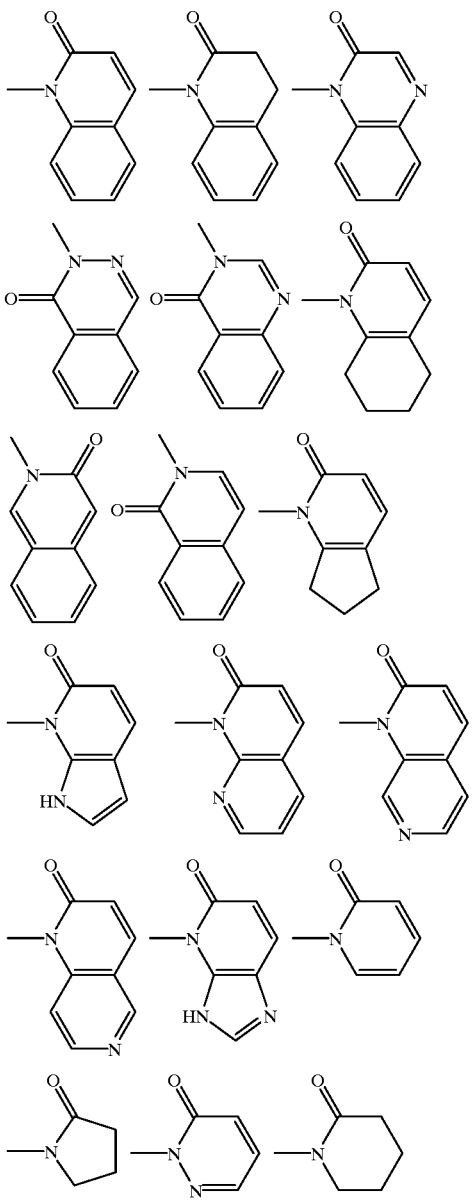

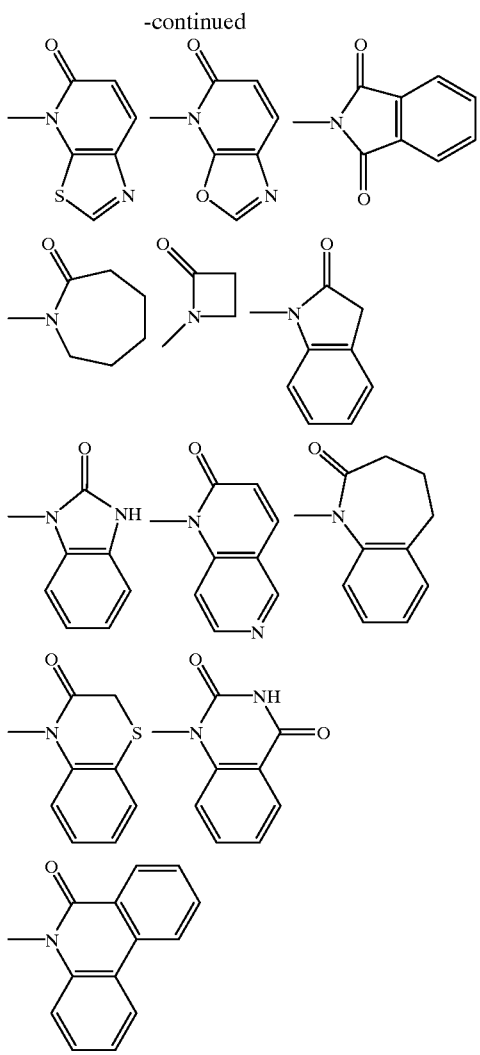

Suitable compounds of the present invention are those of the formula [I] wherein $R^5$ and $R^6$ combine with the adjacent nitrogen atom to form a hetero-cyclic group, for example, (1) an oxo- (or hydroxy-)substituted dihydro- (or tetrahydro-)quinolyl group which may optionally be substituted by a member selected from a mono- or di-lower alkylamino group in which the lower alkyl moiety is optionally substituted by a morpholino group, a monocycloalkyl-substituted amino group, a pyridyl group, an imidazolyl group, a piperidino group or a pyrrolidinyl group; a pyridyl group; a morpholino group; a lower alkyl-substituted triazolyl group; a bis(hydroxy-lower alkyl)aminocarbonyl group; a bis[tri(lower alkyl)silyloxy-lower alkyl]aminocarbonyl group; a morpholino carbonyl group; a lower alkyl-substituted piperazinylcarbonyl group; a hydroxy-lower alkyl-substituted piperazinylcarbonyl group; a tri-lower alkylsilyloxy-lower alkyl-substituted piperazinylcarbonyl group; a lower alkoxycarbonyl group; a carboxyl group; a lower alkyl group; a lower alkoxy group having optionally a hydroxy or lower alkoxy substituent; and a hydroxy group, (2) an oxo- (or hydroxy-)substituted dihydro- (or tetrahydro-)quinoxalinyl group, (3) an oxo- (or hydroxy-) substituted dihydro- (or tetrahydro-)isoquinolyl group which may optionally be substituted by a member selected from a morpholino-substituted lower alkyl group; a lower alkoxy group having optionally a piperidyl, pyridyl or lower alkoxy substituent; and a hydroxy group, (4) an oxo- (or hydroxy-)-substituted dihydro- (or tetrahydro-)phthalazinyl group which may optionally be substituted by a member selected from a lower alkyl group having optionally a pyridyl substituent; a pyrimidinyl group; a lower alkoxy group; a pyridyl group; an imidazolyl group; a phenyl group being optionally substituted by a di-lower alkylamino group or a halogen atom; and a hydroxy group, (5) an oxo- (or hydroxy-)substituted dihydro- (or hexahydro-)pyridyl group which may optionally be substituted by a member selected from a halogen atom; a lower alkyl group; a lower alkoxy group; a nitro group; a pyridyl group; and an imidazolyl group, (6) an oxo- (or hydroxy-)substituted dihydro- (or tetrahydro-) naphthyridinyl group, (7) an oxo- (or hydroxy-) substituted hexahydroquinolyl group, (8) an oxo- (or hydroxy-)substituted dihydroindolyl group, (9) an oxo-(or hydroxy-)substituted dihydro- (or tetrahydro-)benzazepinyl group, (10) a dihydro- (or tetrahydro-)isoquinolyl group, (11) an oxo- (or hydroxy-)-substituted dihydro- (or tetrahydro-)benzothiazinyl group, (12) an oxo- (or hydroxy-)substituted dihydro- (or tetrahydro-)quinazolinyl group which may optionally be substituted by a lower alkyl group and/or an oxo group, (13) an oxo- (or hydroxy-) substituted dihydrobenzimidazolinyl group, (14) an oxo- (or hydroxy-)substituted dihydrophenanthridinyl group, (15) an oxo- (or hydroxy-)-substituted dihydro- (or tetrahydro-) pyrrolyl group which may optionally be substituted by a lower alkyl group, (16) a hexahydropyrazinyl group, (17) a lower alkylenedioxy-substituted hexahydropyridyl group, or (18) a morpholino group.

The oxo- (or hydroxy-)substituted dihydro- (or tetrahydro-)quinolyl group includes specifically an oxo-substituted dihydro- (or tetrahydro-)quinolyl group and a hydroxy-substituted dihydro- (or tetrahydro-)quinolyl group, more specifically an oxo-substituted dihydroquinolyl group, an oxo-substituted tetrahydroquinolyl group, a hydroxy-substituted dihydroquinolyl group, and a hydroxy-substituted tetrahydroquinolyl group. The oxo- (or hydroxy-)-substituted dihydro- (or tetrahydro-)quinoxalinyl group includes specifically an oxo-substituted dihydro- (or tetrahydro-)quinoxalinyl group and a hydroxy-substituted dihydro- (or tetrahydro-)quinoxalinyl group, more specifically an oxo-substituted dihydroquinoxalinyl group, an oxo-substituted tetrahydroquinoxalinyl group, a hydroxy-substituted dihydroquinoxalinyl group, and a hydroxy-substituted tetrahydroquinoxalinyl group. The oxo- (or hydroxy-)-substituted dihydro- (or tetrahydro-)isoquinolyl group includes specifically an oxo-substituted dihydro- (or tetrahydro-)isoquinolyl group, and a hydroxy-substituted dihydro- (or tetrahydro-)isoquinolyl group, more specifically an oxo-substituted dihydroquinolyl group, an oxo-substituted tetrahydroquinolyl group, a hydroxy-substituted dihydroisoquinolyl group, and a hydroxy-substituted tetrahydroisoquinolyl group. The oxo- (or hydroxy-) substituted dihydro- (or tetrahydro-)phthalazinyl group includes specifically an oxo-substituted dihydro- (or tetrahydro-)phthalazinyl group and a hydroxy-substituted dihydro- (or tetrahydro-)phthalazinyl group, more specifically an oxo-substituted dihydrophthalazinyl group, an oxo-substituted tetrahydro-phthalazinyl group, a hydroxy-substituted dihydrophthalazinyl group, and a hydroxy-substituted tetrahydrophthalazinyl group. The oxo- (or hydroxy-)-substituted dihydro- (or hexahydro-)pyridyl group includes specifically an oxo-substituted dihydro- (or hexahydro-)pyridyl group and a hydroxy-substituted dihydro- (or hexahydro-)pyridyl group, more specifically an oxo-substituted dihydropyridyl group, an oxo-substituted hexahydropyridyl group, a hydroxy-substituted dihydropyridyl group, and a hydroxy-substituted hexahydropyridyl group. The oxo- (or hydroxy-)substituted dihydro- (or tetrahydro-)-naphthyridinyl group includes specifically an oxo-substituted dihydro- (or tetrahydro-)naphthyridinyl group and a hydroxy-substituted dihydro- (or tetrahydro-)naphthyridinyl group, more specifically an oxo-substituted dihydronaphthyridinyl group, an oxo-substituted tetrahydronaphthyridinyl group, a hydroxy-substituted dihydronaphthyridinyl group, and a hydroxy-substituted tetrahydronaphthyridinyl group. The oxo- (or hydroxy-)substituted hexahydroquinolyl group includes an oxo-substituted hexahydroquinolyl group and a hydroxy-substituted hexahydroquinolyl group. The oxo- (or hydroxy-)substituted dihydroindolyl group includes an oxo-substituted dihydroindolyl group and a hydroxy-substituted dihydroindolyl group. The oxo- (or hydroxy-)substituted dihydro- (or tetrahydro-)benzazepinyl group includes an oxo-substituted dihydro- (or tetrahydro-)benzazepinyl group and a hydroxy-substituted dihydro- (or tetrahydro-)benzazepinyl group, more specifically an oxo-substituted dihydrobenzazepinyl group, an oxo-substituted tetrahydrobenzazepinyl group, a hydroxy-substituted dihydrobenzazepinyl group, and a hydroxy-substituted tetrahydrobenzazepinyl group. The dihydro-(or tetrahydro-)isoquinolyl group includes a dihydroisoquinolyl group, and a tetrahydroisoquinolyl group. The oxo- (or hydroxy-)substituted dihydro- (or tetrahydro-)benzothiazinyl group includes an oxo-substituted dihydro- (or tetrahydro-)benzothiazinyl group and a hydroxy-substituted dihydro- (or tetrahydro-)benzothiazinyl group, more specifically an oxo-substituted dihydro-benzothiazinyl group, an oxo-substituted tetrahydrobenzothiazinyl group, a hydroxy-substituted dihydrobenzothiazinyl group, and a hydroxy-substituted tetrahydrobenzothiazinyl group. The oxo- (or hydroxy-)substituted dihydro-(or tetrahydro-)quinazolinyl group includes an oxo-substituted dihydro- (or tetrahydro-)quinazolinyl group and a hydroxy-substituted dihydro- (or tetrahydro-)quinazolinyl group, more specifically an oxo-substituted dihydroquinazolinyl group, an oxo-substituted tetrahydroquinazolinyl group, a hydroxy-substituted dihydroquinazolinyl group, and a hydroxy-substituted tetrahydroquinazolinyl group. The oxo- (or hydroxy-)substituted dihydrobenzimidazolinyl group includes an oxo-substituted dihydrobenzimidazolinyl group and a hydroxy-substituted dihydrobenzimidazolinyl group. The oxo- (or hydroxy-)substituted dihydrophenanthridinyl group includes an oxo-substituted dihydrophenanthridinyl group and a hydroxy-substituted dihydro-phenanthridinyl group. The oxo- (or hydroxy-)substituted dihydro- (or tetrahydro-)pyrrolyl group includes an oxo-substituted dihydro- (or tetrahydro-)pyrrolyl group and a hydroxy-substituted dihydro- (or tetrahydro-)pyrrolyl group, more specifically an oxo-substituted dihydropyrrolyl group, an oxo-substituted tetrahydropyrrolyl group, a hydroxy-substituted dihydropyrrolyl group, and a hydroxy-substituted tetrahydropyrrolyl group.

Preferred compounds of the present invention are those of the formula [I] wherein $R^5$ and $R^6$ combine with the adjacent nitrogen atom to form a hetero-cyclic group selected from (I) an oxo-substituted dihydro- (or tetrahydro-)quinolyl group or a hydroxy-substituted dihydro- (or tetrahydro-)quinolyl group, (2) an oxo-substituted dihydro- (or tetrahydro-)quinoxalinyl group, (3) an oxo-substituted dihydro- (or tetrahydro-)isoquinolyl croup, (4) an oxo-substituted dihydro- (or tetrahydro-)phthalazinyl group, (5) an oxo-substituted dihydro- (or hexanydro-)pyridyl group, (6) an oxo-substituted dihydro- (or tetrahydro-)naphthyridinyl group, (7) an oxo-substituted hexahydroquinolyl group, (8) an oxo-substituted dihydroindolyl group, (9) an oxo-substituted dihydro- (or tetrahydro-)benzazepinyl group, (10) a dihydro- (or tetrahydro-)isoquinolyl group, (11) an oxo- substituted dihydro- (or tetrahydro-)benzothiazinyl group, (12) an oxo-substituted dihydro- (or tetrahydro-)quinazolinyl group, (13) an oxo-substituted dihydrobenzimidazolinyl group, (14) an oxo-substituted dihydrophenanthridinyl group, (15) an oxo-substituted dihydro- (or tetrahydro-)pyrrolyl group, (16) a hexahydropyrazinyl group, (17) a lower alkylenedioxy-substituted hexahydropyridyl group, and (18) a morpholino group.

Particularly preferred compounds of the present invention are those of the formula [I] wherein $R^5$ and $R^6$ combine with the adjacent nitrogen atom to form a heterocyclic group selected from (1) an oxo-substituted dihydro- (or tetrahydro-)quinolyl group or a hydroxy-substituted tetrahydroquinolyl group, (2) an oxo-substituted dihydroquinoxalinyl group, (3) an oxo-substituted dihydro-isoquinolyl group, (4) an oxo-substituted dihydrophthalazinyl group, (5) an oxo-substituted dihydro- (or hexahydro-)pyridyl group, (6) an oxo-substituted dihydronaphthyridinyl group, (7) an oxo-substituted hexahydroquinolyl group, (8) an oxo-substituted dihydroindolyl group, (9) an oxo-substituted dihydrobenzazepinyl group, (10) a tetrahydroisoquinolyl group, (11) an oxo-substituted tetrahydrobenzothiazinyl group, (12) an oxo-substituted dihydro- (or tetrahydro-)quinazolinyl group, (13) an oxo-substituted dihydrobenzimidazolinyl group, (14) an oxo-substituted dihydrophenanthridinyl group, (15) an oxo-substituted tetrahydropyrrolyl group, (16) a hexahydropyrazinyl group, (17) a lower alkylenedioxy-substituted hexahydropyridyl group, and (18) a morpholino group.

Among, the compounds [I] of the present invention, the preferred compounds in view of the pharmacological activities are those of the formula [I] wherein $R^5$ and $R^6$ combine with the adjacent nitrogen atom to form a heterocyclic group, which is selected from (1) an oxo-substituted dihydro- (or tetrahydro-)quinolyl or a hydroxy-substituted tetrahydroquinolyl group which may optionally be substituted by a member selected from a mono- or di-lower alkylamino group in which the lower alkyl moiety is substituted by a morpholino group, a monocycloalkylamino group, a pyridyl group, an imidazolyl group, a piperidino group or a pyrrolidinyl group; a pyridyl group; a morpholino group; a lower alkyl-substituted triazolyl group; a lower alkyl-substituted piperazinylcarbonyl group; a lower alkyl group; a lower alkoxy-carbonyl group; a lower alkoxy group having optionally a hydroxy or lower alkoxy substituent; and a hydroxy group, (2) an oxo-substituted dihydroquinoxalinyl group, (3) an oxo-substituted dihydroisoquinolyl group which may optionally be substituted by a member selected from a morpholino-substituted lower alkyl group; a lower alkoxy group having optionally a piperidyl, pyridyl or lower alkoxy substituent; and a hydroxy group, (4) an oxo-substituted dihydrophthalazinyl group which may optionally be substituted by a member selected from a pyridyl-substituted lower alkyl group; a pyrimidinyl group; a pyridyl group; a lower alkoxy group; an imidazolyl group; and a di-lower alkylamino-substituted phenyl group, (5) an oxo-substituted dihydropyridyl group which is substituted by a member selected from a lower alkyl group; a lower alkoxy group; a pyridyl group; and an imidazolyl group, (6) an oxo-substituted dihydronaphthyridinyl group, (7) an oxo-substituted hexahydroquinolyl group, (8) an oxo-substituted dihydroindolyl group, (9) an oxo-substituted tetrahydrobenzothiazinyl group, (10) an oxo-substituted dihydro- (or tetrahydro-)quinazolinyl group which may optionally be substituted by a lower alkyl group and an oxo group, (11) an oxo-substituted dihydrobenzimidazolinyl group, and (12) an oxo-substituted dihydrophenanthridinyl group.

Among the above compounds [I], more preferred compounds in view of the pharmacological activities are those of the formula [I] wherein $R^5$ and $R^6$ combine with the adjacent nitrogen atom to form a heterocyclic group, which is selected from (1) an oxo-substituted dihydro- (or tetrahydro-)quinolyl or a hydroxy-substituted tetrahydroquinolyl group which may optionally be substituted by a member selected from a mono- or di-lower alkylamino group in which the lower alkyl moiety is substituted by a morpholino group, a pyridyl group, an imidazolyl group, a piperidino group or a pyrrolidinyl group; a pyridyl group; a morpholino group; a lower alkyl-substituted triazolyl group; a lower alkyl group; and a lower alkoxy group having optionally a hydroxy or lower alkoxy substituent, (2) an oxo-substituted dihydroquinoxalinyl group, (3) an oxo-substituted dihydroisoquinolyl group which may optionally be substituted by a member selected from a morpholino-substituted lower alkyl group; a lower alkoxy group having a piperidyl or lower alkoxy substituent; and a hydroxy group, (4) an oxo-substituted dihydrophthalazinyl group which may optionally be substituted by a member selected from a pyridyl-substituted lower alkyl group; a pyrimidinyl group; a pyridyl group; a lower alkoxy group; and an imidazolyl group, (5) an oxo-substituted dihydropyridyl group which is substituted by a member selected from a lower alkyl group; a lower alkoxy group; a pyridyl group; and an imidazolyl group, (6) an oxo-substituted tetrahydrobenzothiazinyl group, and (7) an oxo-substituted dihydro- (or tetrahydro-)quinazolinyl group which may optionally be substituted by a lower alkyl group and an oxo group.

Among the above compounds, more preferred compounds in view of the pharmacological activities are those of the formula [I] wherein $R^5$ and $R^6$ combine with the adjacent nitrogen atom to form a heterocyclic group, which is selected from (1) an oxo-substituted dihydroquinolyl or a hydroxy-substituted tetrahydroquinolyl group which may optionally be substituted by a member selected from a mono- or di-lower alkylamino group in which the lower alkyl moiety is substituted by a morpholino group, a pyridyl group, an imidazolyl group, or a piperidino group; a pyridyl group; a morpholino group; a lower alkyl-substituted triazolyl group; and a lower alkoxy group being substituted by a lower alkoxy group or a hydroxy group, (2) an oxo-substituted dihydro-isoquinolyl group which may optionally be substituted by a member selected from a morpholino-substituted lower alkyl group; a lower alkoxy group having a piperidyl or lower alkoxy substituent; and a hydroxy group, (3) an oxo-substituted dihydrophthalazinyl group which may optionally be substituted by a member selected from a pyridyl-substituted lower alkyl group; a pyrimidinyl group; a pyridyl group; a lower alkoxy group; and an imidazolyl group, (4) an oxo-substituted dihydropyridyl group which is substituted by a member selected from a lower alkyl group; a lower alkoxy group; a pyridyl group; and an imidazolyl group, and (5) an oxo-substituted dihydro- (or tetrahydro-)quinazolinyl group which may optionally be substituted by a lower alkyl group and an oxo group.

Among the above compounds, particularly preferred compounds in view of the pharmacological activities are those of the formula [I] wherein $R^5$ and $R^6$ combine with the adjacent nitrogen atom to form a heterocyclic group, which is selected from (1) an oxo-substituted dihydroquinolyl group which may optionally be substituted by a member selected from a mono- or di-lower alkylamino group in which the lower alkyl moiety is substituted by a morpholino group, a pyridyl group, an imidazolyl group, or a piperidino group; a pyridyl group; a morpholino group; a lower alkyl-substituted triazolyl group; and a lower alkoxy group being substituted by a lower alkoxy group or a hydroxy group, (2) an oxo-substituted dihydroisoquinolyl group which may optionally be substituted by a member selected from a morpholino-substituted lower alkyl group and a piperidyl-substituted lower alkoxy group, (3) an oxo-substituted dihydrophthalazinyl group which may optionally be substituted by a member selected from a pyridyl-substituted lower alkyl group; a pyrimidinyl group; a pyridyl group; a lower alkoxy group; and an imidazolyl group, and (4) an oxo-substituted dihydropyridyl group which is substituted by a member selected from a lower alkyl group, a lower alkoxy group and an imidazolyl group.

Among the compounds [I] of the present invention, other preferred compounds in view of the pharmacological activities are those of the formula [I] wherein $R^5$ and $R^6$ combine with the adjacent nitrogen atom to form a hetero-cyclic group, which is selected from (1) an oxo-substituted dihydro- (or tetrahydro-)quinolyl or hydroxy-substituted tetrahydroquinolyl group which may optionally be substituted by a member selected from a mono- or di-lower alkylamino group in which the lower alkyl moiety is substituted by a morpholino group, a monocycloalkyl-substituted amino group, a pyridyl group, an imidazolyl group, or a piperidino group; a pyridyl group; a morpholino group; a lower alkyl-substituted piperazinylcarbonyl group; a lower alkoxycarbonyl group; a lower alkyl group; a hydroxy group; and a lower alkoxy group having optionally a hydroxy or lower alkoxy substituent, (2) an oxo-substituted dihydroisoquinolyl group which may optionally be substituted by a member selected from a morpholino-substituted lower alkyl group; and a lower alkoxy group having a piperidyl, pyridyl or lower alkoxy substituent, (3) an oxo-substituted dihydrophthalazinyl group which may optionally be substituted by a member selected from a pyridyl-substituted lower alkyl group; a pyrimidinyl group; a lower alkoxy; a pyridyl group; an imidazolyl group; and a di-lower alkylamino-substituted phenyl group, (4) an oxo-substituted dihydropyridyl group which is substituted by a pyridyl group, (5) an oxo-substituted dihydronaphthyridinyl group, (6) an oxo-substituted hexahydroquinolyl group, (7) an oxo-substituted dihydroindolyl group, (8) an oxo-substituted tetrahydrobenzothiazinyl group, (9) an oxo-substituted dihydro- (or tetrahydro-)quinazolinyl group which may optionally be substituted by a lower alkyl group and an oxo group, (10) an oxo-substituted dihydrobenzimidazolinyl group, and (11) an oxo-substituted dihydrophenanthridinyl group.

Among the above compounds, more preferred compounds in view of the pharmacological activities are those of the formula [I] wherein $R^5$ and $R^6$ combine with the adjacent nitrogen atom to form a heterocyclic group, which is selected from (1) an oxo-substituted dihydro- (or tetrahydro-)quinolyl group which may optionally be substituted by a member selected from a mono- or di-lower alkylamino group in which the lower alkyl moiety is substituted by a morpholino group, an imidazolyl group or a pyridyl group; a morpholino group; and a lower alkyl group, (2) an oxo-substituted dihydroisoquinolyl group which may optionally be substituted by a member selected from a morpholino-substituted lower alkyl group and a lower alkoxy group having a pyridyl or lower alkoxy substituent, (3) an oxo-substituted dihydrophthalazinyl group which is substituted by a member selected from a pyridyl-substituted lower alkyl group; a lower alkoxy group; a pyridyl group; and a di-lower alkylamino-substituted phenyl group, and (4) an oxo-substituted dihydrophenanthridinyl group.

Among the above compounds, particularly preferred compounds in view of the pharmacological activities are those of the formula [I] wherein $R^5$ and $R^6$ combine with the adjacent nitrogen atom to form a heterocyclic group, which is selected from (1) an oxo-substituted dihydro- (or tetrahydro-)quinolyl group which may optionally be substituted by a member selected from a mono- or di-lower alkylamino group in which the lower alkyl moiety is substituted by a pyridyl group; a morpholino group; and a lower alkyl group, (2) an oxo-substituted dihydroisoquinolyl group which may optionally be substituted by a member selected from a morpholino-substituted lower alkyl group and a lower alkoxy group having a pyridyl or lower alkoxy substituent, (3) an oxo-substituted dihydrophthalazinyl group which is substituted by a member selected from a pyridyl-substituted lower alkyl group; a lower alkoxy; a pyridyl group; and a di-lower alkylamino-substituted phenyl group, and (4) an oxo-substituted dihydrophenanthridinyl group.

Among the compounds [I] of the present invention, other preferred compounds in view of the pharmacological activities are those of the formula [I] wherein $R^5$ and $R^6$ combine with the adjacent nitrogen atom to form a hetero-cyclic group, which is selected from (1) an oxo-substituted dihydro- (or tetrahydro-)quinolyl group which may optionally be substituted by a member selected from a mono- or di-lower alkylamino group in which the lower alkyl moiety is substituted by a morpholino group, a pyridyl group or an imidazolyl group; a morpholino group; and a lower alkyl group, (2) an oxo-substituted dihydroisoquinolyl group which is substituted by a member selected from a morpholino-substituted lower alkyl group; and a lower alkoxy-substituted lower alkoxy group, and (3) an oxo-substituted dihydrophthalazinyl group which is substituted by a member selected from a pyridyl-substituted lower alkyl group; a pyridyl group; and a lower alkoxy group.

Still further preferred compounds in view of the pharmacological activities are those of the formula [I] wherein $R^5$ and $R^6$ combine with the adjacent nitrogen atom to form a heterocyclic group of the following formula:

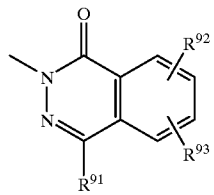

wherein $R^{91}$, $R^{92}$, and $R^{93}$ are the same or different and are each a hydrogen atom, a hydroxy group, a lower alkoxy group, a lower alkyl group having optionally a pyridyl substituent, a phenyl group being optionally substituted by a di-lower alkylamino group or a halogen atom, a pyridyl group, a pyrimidinyl group, or an imidazolyl group (hereinafter, the above compounds are referred to as "compounds [I-a]").

Among the above compounds, more preferred compounds in view of the pharmacological activities are those of the formula [π wherein $R^{91}$, $R^{92}$ and $R^{93}$ are the same or different and are each a hydrogen atom, a lower alkoxy group, a pyridyl-substituted lower alkyl group, a di-lower alkylaminophenyl group or a pyridyl group.

Among the above-mentioned preferred compounds [I] in view of the pharmacological activities, much more preferred compounds are those of the formula [I] wherein $R^1$ and $R^2$ are the same or different and are each a lower alkoxy group, and $R^3$ and $R^4$ are each a hydroxy-substituted methyl group.

The compounds [I] of this invention may exist in the form of an optical isomer owing to the asymmetric carbon, and those optical isomers and a mixture thereof are also inclusive in this invention.

The desired compounds [I] of this invention can be used as a medicament either in the free form or in the form of a pharmaceutically acceptable salt. The pharmaceutically acceptable salt includes, for example, a salt with an inorganic acid, such as hydrochloride, sulfate, or hydrobromide, and a salt with an organic acid, such as acetate, fumarate, oxalate, methanesulfonate, or maleate. Besides, when the compounds of this invention contain such a substituent as a carboxyl croup, they may be in the form of a salt with a base, such as an alkali metal (e.g. sodium salt, potassium salt), or an alkaline earth metal (e.g. calcium salt). Thus, the compounds [I] and salts thereof of this invention are inclusive any internal salts, addition products, solvates, or hydrates.

The compounds [I] or salts thereof may be administered orally or parenterally. The compounds can be administered in the form of a pharmaceutical preparation such as tablets, granules, capsules, powders, injections, and inhalants by a conventional method.

The dosage of the compounds [I] or pharmaceutically acceptable salts thereof of this invention may vary depending on the administration routes, the age, body weight and conditions of the patients, etc. but may be in the range of about 0.001 to 10 mg/kg per day, preferably about 0.003 to 3 mg/kg per day.

The compounds [I] and salts of this invention can be prepared by the following Processes [A] to [C].

Process A

The compounds [I] can be prepared by reacting a compound of the formula [II]:

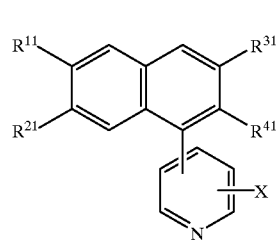

wherein $R^{11}$ and $R^{21}$ are the same or different and are each a hydrogen atom or a protected or unprotected hydroxy group, either one of $R^{31}$ and $R^{41}$ is a protected or unprotected hydroxy-substituted methyl group, and another one is a hydrogen atom, a lower alkyl group, or a protected or unprotected hydroxy-substituted methyl group, and X is a halogen atom, with a nitrogen-containing compound of the formula [III]:

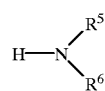

wherein $R^5$ and $R^6$ are the same as defined above, and where $R^{11}$ and/or $R^{21}$ are a protected hydroxy group and $R^{31}$ and/or $R^{41}$ are a protected hydroxy-substituted methyl group, optionally followed by removing protecting groups for the hydroxy groups, partially or wholly depending on the kinds of the protecting group, and if necessary, re-protecting the hydroxy group(s) at 6- and/or 7-positions or the hydroxymethyl moieties at 2- and/or 3-positions, and further if necessary, protecting whole hydroxy groups or hydroxymethyl moieties.

Process B

Among the compounds [I] of this invention, the compounds of the formula [I']:

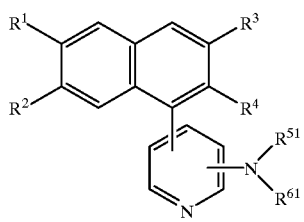

wherein $R^{51}$ and $R^{61}$ combine together with the adjacent nitrogen atom to form a heterocyclic group having at least one oxo substituent, and other symbols are the same as defined above, can be prepared by reacting a compound of the formula [IV]:

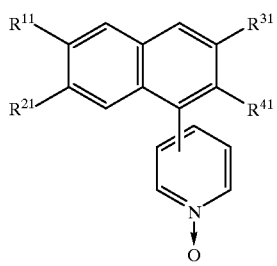

wherein the symbols are the same as defined above, with a nitrogen-containing compound of the formula [V]:

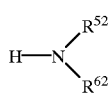

wherein $R^{52}$ and $R^{62}$ combine together with the adjacent nitrogen atom to form a heterocyclic group having at least one halogen substituent, and where $R^{11}$ and/or $R^{21}$ are a protected hydroxy group and $R^{31}$ and/or $R^{41}$ are a protected hydroxy-substituted methyl group, optionally followed by removing protecting groups for the hydroxy groups, partially or wholly depending on the kinds of the protecting group, and if necessary, re-protecting the hydroxy group(s) at 6- and/or 7-positions or the hydroxymethyl moieties at 2- and/or 3-positions, and further if necessary, protecting whole hydroxy groups or hydroxymethyl moieties.

Process C

Among the compounds [I] of this invention, the compounds of the formula [I"]:

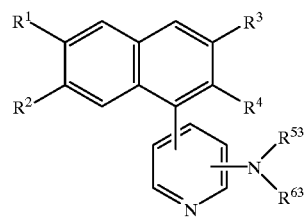

wherein $R^{53}$ and $R^{63}$ are the same or different and are each a hydrogen atom, a substituted or unsubstituted alkyl group, a substituted or unsubstituted phenyl group, or a protected or unprotected amino group, or both combine together with the adjacent nitrogen atom to form a heterocyclic group being optionally substituted and being stable to a reduction reaction, and other symbols are the same as defined above, can be prepared by subjecting a compound of the formula [VI]:

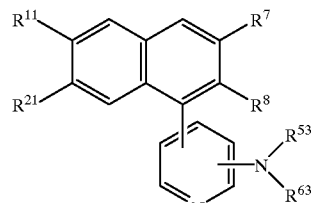

wherein either one of $R^7$ and $R^8$ is a free or esterified carboxyl group, and another one is a hydrogen atom, a lower alkyl group, or a free or esterified carboxyl group, and other symbols are the same as defined above, or an internal acid anhydride compound thereof to reduction, and where $R^{11}$ and/or $R^{21}$ are a protected hydroxy group, optionally followed by removing protecting groups for the hydroxy groups, and if necessary, re-protecting the hydroxy group(s) at 6- and/or 7-positions or the hydroxymethyl moieties at 2- and/or 3-positions, and further if necessary, protecting whole hydroxy groups or hydroxymethyl moieties.

These Processes A to C are carried out in the following matter.

Process A

The reaction of the compound [II] and the compound [III] is carried out in the presence of a base and a copper catalyst in an appropriate solvent. Suitable examples of the base are an alkali metal hydride and an alkali metal carbonate, and the copper catalyst is preferably copper (I) iodide, copper (I) bromide, copper (II) bromide, copper (0) bronze, copper (II) oxide, and the like. The solvent is, for example, dimethylformamide, dimethyl sulfoxide, dimethylacetamide, toluene, xylene, etc. The reaction is preferably carried out at 80° to 160° C., more preferably at 120 to 150° C.

Process B

The reaction of the compound [IV] and the halogenonitrogen containing compound [V] can be carried out in the presence or absence of an acid catalyst in an appropriate solvent. Suitable examples of the acid catalyst are hydrogen bromide, hydrogen chloride, acetic acid. The solvent is, for example, dimethylformamide, dimethyl sulfoxide, toluene, xylene, mesitylene, di-, tri- or tetra-chloroethane, etc. The reaction is preferably carried out at 80° to 160° C., more preferably at 110° to 150° C.

Process C

The reduction reaction of the compound [VI] or its internal acid anhydride compound can be carried out with an appropriate reducing agent in a solvent. The esterified carboxyl group in the compound [VI] may be any group which can be converted into a hydroxymethyl group by the reduction, for example, a lower alkoxycarbonyl group. Suitable reducing agent may be selected depending on the kinds of the $R^7$ and $R^8$. For example, when the $R^7$ and $R^8$ are an esterified carboxyl group, the suitable reducing agent is a metal hydride (e.g. lithium aluminum hydride, sodium bis (methoxyethoxy)aluminum hydride, sodium borohydride, etc., more preferably sodium borohydride. In the case of sodium borohydride, this reaction is preferably carried out in an appropriate solvent, for example, in a mixture of an ether (e.g. tetrahydrofuran, diethyl ether) and a lower alkanol, with heating. When the $R^7$ and/or $R^8$ are a free carboxyl group, the suitable reducing agent is lithium aluminum hydride. The internal acid anhydride compound of the compound [VI] is prepared by subjecting a compound [VI] wherein $R^7$ and $R^8$ are a free carboxyl group to an internal dehydration reaction, and the reduction of said internal acid anhydride compound can be carried out in the same manner as in the above reduction of the compound [VI] wherein $R^7$ and/or $R^8$ are a free carboxyl group. These reactions may be carried out in an appropriate solvent, for example, an ether (e.g. tetrahydrofuran, diethyl ether, dioxane) under cooling.

In the above Processes A, B and C., where $R^{11}$ and/or $R^{21}$ are a protected hydroxy group and $R^{31}$ and/or $R^{41}$ are a protected hydroxy-substituted methyl group, the removal of the protecting groups from the product is carried out by a conventional method such as hydrolysis, treatment with an acid, or reduction, which is selected depending on the kinds of the protecting group. Besides, in the above Processes A, B and C, the protection of the hydroxy group(s) at 6- and/or 7-positions or the hydroxymethyl moieties at 2- and/or 3-positions may be carried out by condensing with an anhydride or halide of a lower alkanoic acid or a cycloalkanoic acid, a lower alkyl halide having optionally a lower alkoxycarbonyl substituent, or a protected or unprotected carboxy-substituted lower alkyl sulfonate, which corresponds to the protecting group in $R^1$ and $R^2$ as well as in $R^3$ and $R^4$, in a conventional manner. The reaction may preferably be carried out in the presence of a base (e.g. triethylamine, pyridine, dimethyl-aminopyridine, sodium hydride, hexamethylphosphoric triamide, etc.) in an appropriate solvent (e.g. methylene chloride, tetrahydrofuran, etc.) or without solvent The protection may also be carried out by reacting each product with a protected or unprotected amino-substituted lower alkylcarboxylic acid which corresponds to the protecting group in $R^1$ and $R^2$ as well as in $R^3$ and $R^4$. This reaction may be carried out in the presence of a condensation agent (e.g. dicyclohexylcarbodiimide, water-soluble carbodiimide derivatives) in an appropriate solvent (e.g. dimethylformamide, methylene chloride, chloroform). In this case, the hydroxymethyl moiety at 3-position is more sensitive to said reaction than the hydroxymethyl moiety at 2-position, and hence, when the lower alkanoic acid anhydride or halide, or a lower alkyl halide is used in an amount of equimolar to one mole of the product, there is mainly obtained the desired product wherein only the hydroxymethyl moiety at 3-position is protected, and when the former is used in an amount of two or more moles to one mole of the latter, there is obtained the product wherein both groups at 2-position and 3-position are protected. The protecting group for the carboxyl group and/or amino group includes any conventional protecting group for carboxyl group and/or amino group, and those protecting groups may also be removed by a conventional method.

The desired compounds [I] of this invention obtained by the above processes may be converted into other desired compounds [I] by mutual conversion. Such a mutual conversion reaction may be selected so as to make fit each compound depending on the kinds of the substituents of the compounds. For example, it may be carried out as follows.

The compounds [I-a] can be prepared by reacting a compound of the formula [I] wherein the corresponding, $R^5$ is-a hydrogen atom and $R^6$ is an amino group (hereinafter, this compound is referred to as "compound [I-b]") or a salt thereof, with a carboxylic acid compound of the formula [VII]:

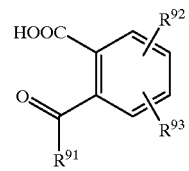

[VII]

or a salt thereof, wherein the symbols are the same as defined above.

Besides, the compound [I-a] wherein $R^{91}$ is a hydroxy group can be prepared by reacting a compound [I-b] or a salt thereof, with an acid anhydride compound of the formula [VIII]:

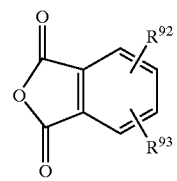

[VIII]

wherein the symbols are the same as defined above.

The above reactions can preferably be carried out in an appropriate solvent (e.g. a lower alkanol, ethylene glycol, dioxane, toluene, etc.) at 100–140° C.

The starting compounds [II] used in this invention are novel compounds and are prepared, for example, by treating a benzaldehyde compound of the formula [IX]:

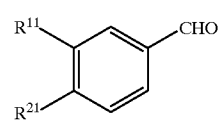

[IX]

wherein the symbols are the same as defined above, with a halogen (e.g. bromine), reacting the resulting 6-halogenobenzaldehyde with methyl orthoformate in the presence of an acid catalyst (e.g. strongly acidic resin, etc.), reacting the product with an aldehyde compound of the formula [X]:

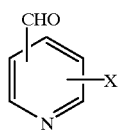
[X]

wherein X is the same as defined above, in the presence of a base (e.g. n-butyl-lithium, etc.), condensing the resulting compound with an olefin compound of the formula [XI]:

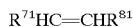
[XI]

wherein either one of the $R^{71}$ and $R^{81}$ is an esterified carboxyl group, and another one is a hydrogen atom, a lower alkyl group or an esterified carboxyl group, to give a compound of the formula [XII]:

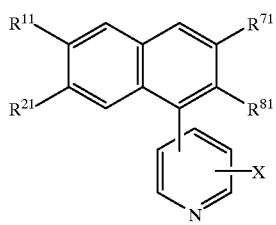
[XII]

wherein the symbols are the same as defined above, and then reducing this product with a reducing agent (e.g. an alkali metal borohydride, sodium bis(methoxyethoxy)aluminum hydride, etc.).

Alternatively, the starting compounds [II] may also be prepared by using a compound of the formula [XIII]:

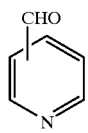
[XIII]

instead of the compound [X] in the above process to give a compound of the formula [XIV]:

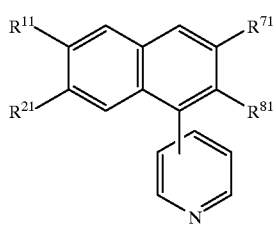
[XIV]

wherein the symbols are the same as defined above, oxidizing this product with an oxidizing agent (e.g. meta-chloroperbenzoic acid, hydrogen peroxide, potassium peroxymonosulfate ($2KHSO_5 \cdot KHSO_4 \cdot K_2SO_4$), etc.) to give a compound of the formula [XV]:

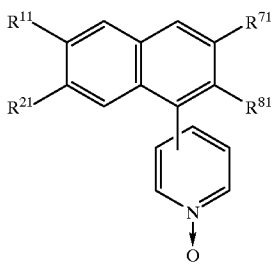
[XV]

wherein the symbols are the same as defined above, treating this product with a halogenating agent (e.g. phosphorus oxychloride, phosphorus oxybromide, etc.) to give a compound of the formula [XII], and then reducing this product with a reducing agent (e.g. an alkali metal borohydride, sodium bis(methoxyethoxy)aluminum hydride, etc.).

Moreover, the compound of the formula [XIV] wherein $R^{71}$ is an esterified carboxyl group and $R^{81}$ is a hydrogen atom may be prepared by reacting a compound [XIII] with a protected acrylic acid, wherein the carboxyl group is protected by a conventional protecting group (e.g. tert-butyl group, benzyl group, etc.), optionally followed by removing the protecting group for the carboxyl group by a conventional method to give a compound of the formula:

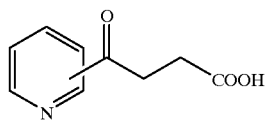

reacting this product with a benzaldehyde of the formula [IX] and acetic anhydride in the presence of sodium acetate (or sulfur trioxide in the presence of N,N-dimethylformamide) to give a compound of the formula [XVI]:

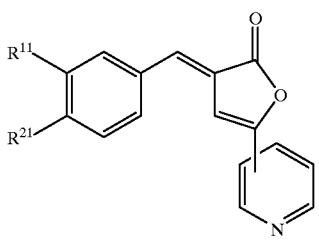
[XVI]

wherein the symbols are the same as defined above, subjecting the compound of naphthalene to a reaction with an acid catalyst (e.g. a mixture of acetic acid-hydrochloric acid or aluminum chloride), and finally esterifying the carboxyl group at 3-position of the naphthalene ring by a conventional method.

The starting compound [IV] used in this invention may be prepared, for example, by reducing a compound of the formula [XIV] with a reducing agent (e.g. sodium bis (methoxyethoxy)aluminum hydride), protecting the hydroxy group of the resulting 2,3-bis(hydroxymethyl) compound, oxidizing the resulting compound with an oxidizing agent (e.g. meta-chloroperbenzoic acid), and if desired, removing the protecting group of the hydroxy croup in the product.

The intermediate compounds [VI] are also novel compounds and can be prepared by reacting the compound [XII]

with the nitrogen-containing compound [III] in the same manner as in the reaction of the compound [II] and the compound [III] described hereinabove. The compound [VI] may also be prepared by reacting the compound [XV] with the halogeno-nitrogen-containing compound [V] in the same manner as in the reaction of the compound [IV] with the halogeno-nitrogen-containing compound [V].

In the present specification and claims, the alkyl group includes a straight chain or branched chain alkyl group having 1 to 16 carbon atoms, preferably ones having 1 to 8 carbon atoms. The lower alkyl group and the lower alkoxy group include a straight chain or branched chain alkyl or alkoxy group having 1 to 6 carbon atoms, preferably ones having 1 to 4 carbon atoms, respectively. The lower alkenyl group, the lower alkynyl group, the lower alkylenedioxy group and the lower alkanoyl group include a straight chain or branched chain ones having 2 to 7 carbon atoms, preferably ones having 2 to 5 carbon atoms, respectively. The cycloalkyl group includes ones having 3 to 8 carbon atoms, preferably 3 to 6 carbon atoms. The halogen atom is chlorine atom, bromine atom, fluorine atom, or iodine atom.

The present invention is illustrated in detail by the following Examples and Reference Examples, but should not be construed to be limited thereto. Besides, the compounds [I] of the present invention prepared by the above mentioned Processes or by modified processes thereof are exemplified in the following Tables 1 to 14.

TABLE 1

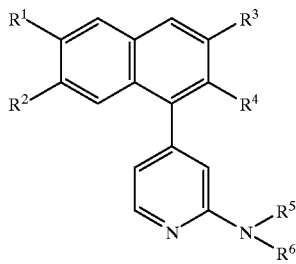

| Ex. No. | R¹ | R² | R³ | R⁴ | —NR⁵R⁶ | Physical properties |
|---|---|---|---|---|---|---|
| 1 | —OC₂H₅ | —OC₂H₅ | —CH₂O—COCH₃ | —CH₂O—COCH₃ | 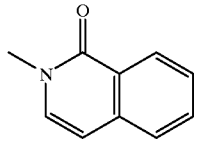 | M.p. 90–93° C. |
| 2 | —OCH₃ | —OCH₃ | —CH₂O—COCH₃ | —CH₂O—COCH₃ | 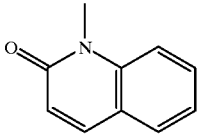 | M.p. 181–184° C. |
| 3 | —OCH₃ | —OCH₃ | —CH₂O—COCH₃ | —CH₂O—COCH₃ | 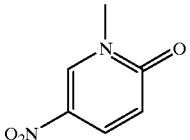 | M.p. 81–84° C. |
| 4 | —OC₂H₅ | —OC₂H₅ | —CH₂OH | —CH₂OH | 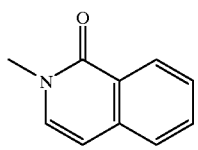 | M.p. 131–134° C. |
| 5 | —OCH₃ | —OCH₃ | —CH₂OH | —CH₂OH | 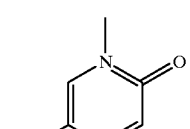 | M.p. 248–251° C. (decomposed) |

TABLE 2
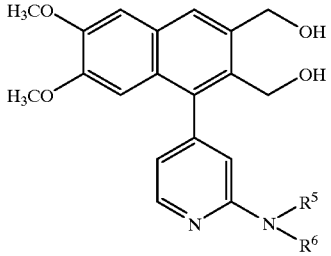
| Ex. No. | —NR⁵R⁶ | Physical properties |
|---|---|---|
| 6 | 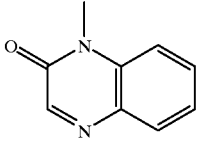 | M.p. 158–165° C. (decomposed) |
| 7* | 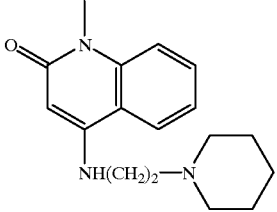 | M.p. >220° C. |
| 8 | 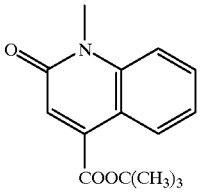 | M.p. 190–193° C. |
| 9 | 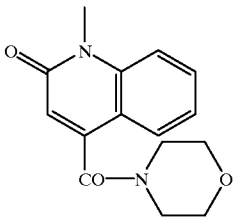 | M.p. 183–186° C. |
| 10* | 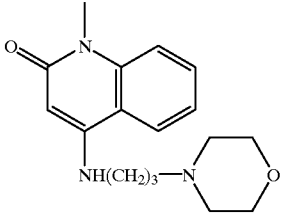 | M.p. >220° C. |

TABLE 2-continued
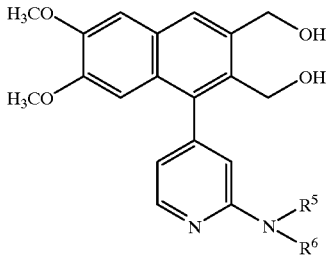
| Ex. No. | —NR⁵R⁶ | Physical properties |
|---|---|---|
| 11* |  | M.p. >220° C. |
| 12* | 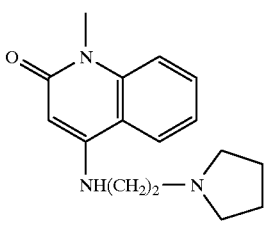 | M.p. 180–187° C. (decomposed) |
| 13* | 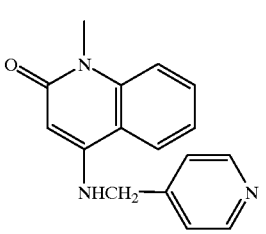 | M.p. >220° C. |
| 14* | 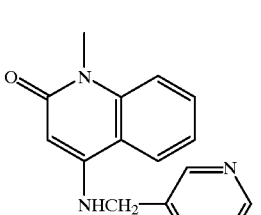 | M.p. 190–200° C. (decomposed) |
| 15* | 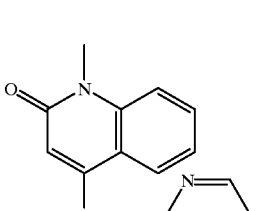 | M.p. 185–192° C. (decomposed) |

TABLE 2-continued
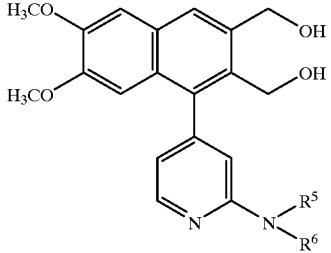
| Ex. No. | —NR⁵R⁶ | Physical properties |
|---|---|---|
| 16* | 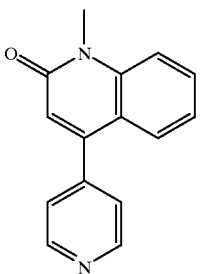 | M.p. 247–249° C. (decomposed) |
| 17* | 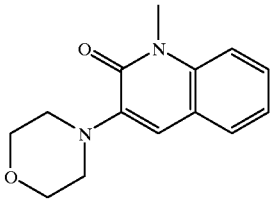 | M.p. 193–195° C. (decomposed) |
| 18* | 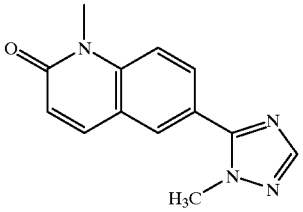 | M.p. 214–217° C. (decomposed) |
| 19 | 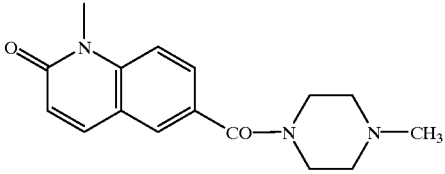 | M.p. 168–171° C. |
| 20 |  | M.p. 58–61° C. |

TABLE 2-continued

| Ex. No. | —NR⁵R⁶ | Physical properties |
|---|---|---|
| 21 | (1-methyl-2-oxo-1,2-dihydroquinolin-4-yl)carbonyl-piperazine-N-(CH₂)₂OSi(CH₃)₂C(CH₃)₃ | M.p. 107–110° C. |
| 22 | 2-methyl-5-(OCH₂OCH₃)-1(2H)-isoquinolinone | M.p. 99–102° C. |
| 23* | 2-methyl-5-(O(CH₂)₂-piperidinyl)-1(2H)-isoquinolinone | M.p. 175–178° C. (decomposed) |
| 24* | 2-methyl-5-(O(CH₂)₂-morpholinyl)-1(2H)-isoquinolinone | M.p. 201–203° C. (decomposed) |
| 25* | 2-methyl-5-(OCH₂-3-pyridyl)-1(2H)-isoquinolinone | M.p. 97–99° C. |

TABLE 2-continued

| Ex. No. | —NR⁵R⁶ | Physical properties |
|---|---|---|
| 26 | 5-chloro-1-methyl-pyridin-2(1H)-one | M.p. 197–199° C. |
| 27 | 6-methyl-4-methyl-1-methyl-pyridin-2(1H)-one | M.p. 114–116° C. |
| 28 | 5-ethyl-1-methyl-pyridin-2(1H)-one | M.p. 191–193° C. |
| 29 | 4-methyl-1-methyl-pyridin-2(1H)-one | M.p. 66–69° C. |
| 30 | 6-chloro-1-methyl-pyridin-2(1H)-one | M.p. 166–168° C. |
| 31 | 3,5-dimethyl-1-methyl-pyridin-2(1H)-one | M.p. 158–161° C. |
| 32 | 3-ethyl-1-methyl-pyridin-2(1H)-one | M.p. 154–157° C. |

TABLE 2-continued

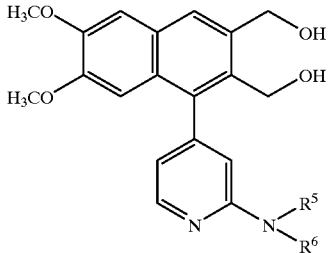

| Ex. No. | —NR⁵R⁶ | Physical properties |
|---|---|---|
| 33 | (1-methyl-3-methoxy-2-oxo-1,2-dihydropyridin-yl) | M.p. 200–202° C. (decomposed) |
| 34 | (1-methyl-4-tert-butyl-2-oxo-1,2-dihydropyridin-yl) | M.p. 246–249° C. |
| 35* | (1-methyl-2-oxo-4-(pyridin-4-yl)-1,2-dihydropyridin-yl) | M.p. 256–259° C. (decomposed) |
| 36* | (1-methyl-2-oxo-4-(pyridin-2-yl)-1,2-dihydropyridin-yl) | M.p. 151–153° C. (decomposed) |
| 37* | (1-methyl-4-(imidazol-1-yl)-2-oxo-1,2-dihydropyridin-yl) | M.p. >250° C. |
| 38 | (1-methyl-2-oxo-1,2-dihydro-1,8-naphthyridin-yl) | M.p. 275–278° C. (decomposed) |
| 39 | (1-methyl-2-oxo-1,2-dihydro-1,6-naphthyridin-yl) | M.p. 243–246° C. (decomposed) |
| 40 | (1-methyl-2-oxo-1,2,3,4-tetrahydroquinolin-yl) | M.p. 132–135° C. |

TABLE 2-continued
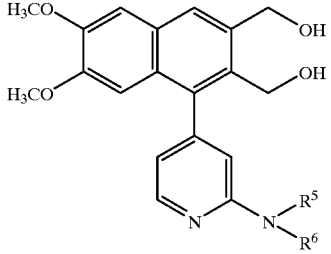
| Ex. No. | —NR⁵R⁶ | Physical properties |
|---|---|---|
| 41 | | M.p. 71–74° C. |
| 42 | | M.p. 173–175° C. |
| 43 | | M.p. 245–248° C. (decomposed) |
| 44 | | M.p. 152–154° C. |
| 45 | | M.p. 168–171° C. |
| 46 | | M.p. 113–115° C. |

TABLE 2-continued
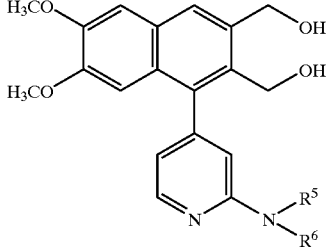
| Ex. No. | —NR⁵R⁶ | Physical properties |
| --- | --- | --- |
| 47 | 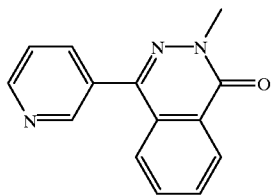 | M.p. 201–203° C. |
| 48* | 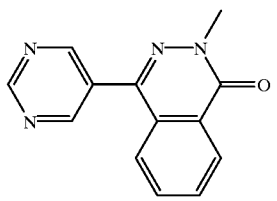 | M.p. 212–215° C. (decomposed) |
| 49* | 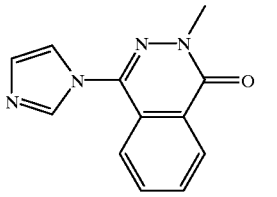 | M.p. 172–175° C. (decomposed) |
| 50* | 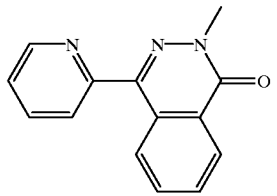 | M.p. >250° C. |
| 51* | | M.p. 162–164° C. (decomposed) |

TABLE 2-continued
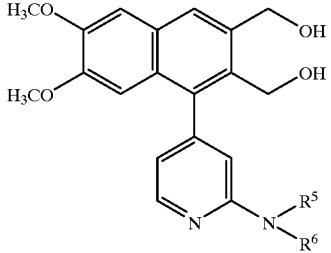
| Ex. No. | —NR⁵R⁶ | Physical properties |
|---|---|---|
| 52* | 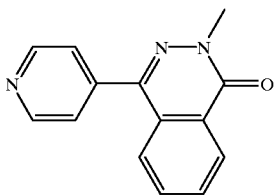 | M.p. >250° C. |
| 53* | 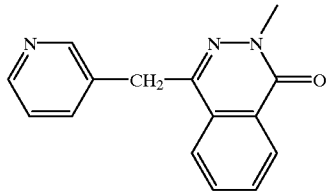 | M.p. >250° C. |
| 54 | 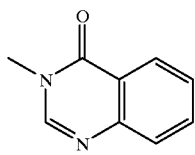 | M.p. 201–203° C. |
| 55 | 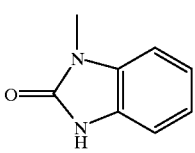 | M.p. 265–268° C. |
| 56 | 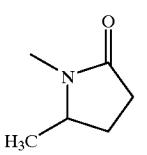 | M.p. 51–54° C. |
| 57 | 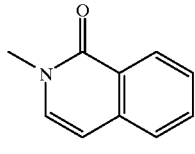 | M.p. 210–212° C. |
*Hydrochloride

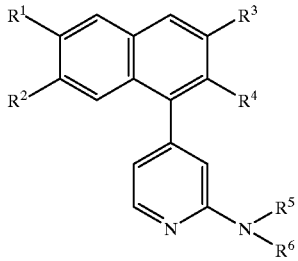

TABLE 5
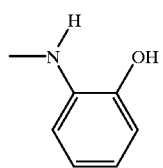
| Ex. No. | —NR⁵R⁶ | Physical properties |
|---|---|---|
| 63 | (1-methyl-2-oxo-1,2-dihydroquinolin-yl) | M.p. 142–143° C. |
TABLE 6
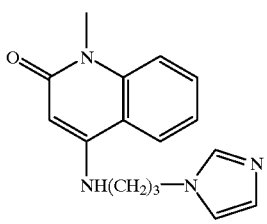
| Ex. No. | R¹ | R² | —NR⁵R⁶ | Physical properties |
|---|---|---|---|---|
| 64 | —OCH₃ | —OCH₃ | —NH₂ | M.p. 99–103° C. |
| 65 | —OCH₃ | —OCH₃ | —NH—(2-hydroxyphenyl) | M.p. 90–93° C. |
| 66 | —OCH₃ | —OCH₃ | (1-methyl-2-oxo-1,2-dihydroquinolin-yl) | M.p. >230° C. |
| 67* | —OCH₃ | —OCH₃ | (1-methyl-2-oxo-4-[NH(CH₂)₃-1-imidazolyl]-1,2-dihydroquinolin-yl) | M.p. >220° C. |

TABLE 6-continued
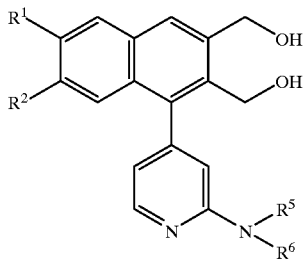
| Ex. No. | R¹ | R² | —NR⁵R⁶ | Physical properties |
|---|---|---|---|---|
| 68 | —OC$_2$H$_5$ | —OC$_2$H$_5$ | 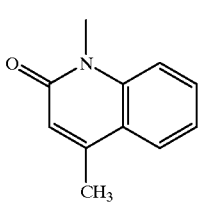 | M.p. >230° C. |
| 69 | —OCH$_3$ | —OCH$_3$ | 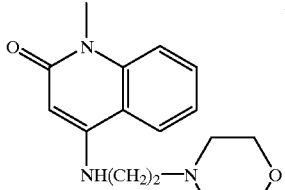 | M.p. 150–158° C. (decomposed) |
| 70 | —OCH$_3$ | —OCH$_3$ | 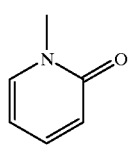 | M.p. 205–208° C. |
| 71 | —OC$_2$H$_5$ | —OC$_2$H$_5$ | 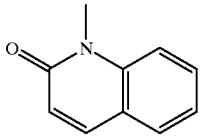 | M.p. 195–196° C. |
| 72 | —OC$_2$H$_5$ | —OC$_2$H$_5$ | 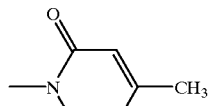 | M.p. 172–175° C. |
| 73 | —OCH$_3$ | —OCH$_3$ | 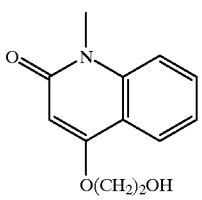 | M.p. 100–110° C. (decomposed) |

TABLE 6-continued
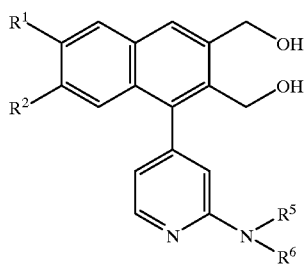
| Ex. No. | R¹ | R² | —NR⁵R⁶ | Physical properties |
|---|---|---|---|---|
| 74 | —OCH₃ | —OCH₃ | | M.p. 204–207° C. |
| 75 | —OCH₃ | —OCH₃ | | M.p. 183–185° C. |
| 76 | —OCH₃ | —OCH₃ | | M.p. >220° C. |
| 77 | —OCH₃ | —OCH₃ | | M.p. 68–70° C. |
| 78 | —OCH₃ | —OCH₃ | | M.p. 204–206° C. |
| 79 | —OCH₃ | —OCH₃ | | M.p. 195–196° C. |

TABLE 6-continued

| Ex. No. | R¹ | R² | —NR⁵R⁶ | Physical properties |
|---|---|---|---|---|
| 80 | —OCH₃ | —OCH₃ | *N-methyl-5,6,7,8-tetrahydroquinolin-2(1H)-one* | M.p. 205–207° C. |

TABLE 7

| Ex. No. | —NR⁵R⁶ | Physical properties |
|---|---|---|
| 81 | *2-methylisoquinolin-3(2H)-one* | M.p. 75–78° C. |
| 82 | *1-methyl-4-hydroxy-1,2,3,4-tetrahydroquinoline* | M.p. 90–94° C. |
| 83 | —N(H)—CH(CH₃)CH₂CH₂CH₂OH | M.p. 57–61° C. |
| 84 | —N(H)—(2-hydroxypropyl)phenyl (CH₂CH₂CH₂OH) | M.p. 156–158° C. |

TABLE 7-continued

| Ex. No. | —NR⁵R⁶ | Physical properties |
|---|---|---|
| 85 | *1-methyl-4-hydroxyquinolin-2(1H)-one* | M.p. 160–170° C. |
| 86 | *2-methyl-5-hydroxyisoquinolin-1(2H)-one* | M.p. 138–140° C. |
| 87 | *1-methyl-4-carboxyquinolin-2(1H)-one* | M.p. >250° C. |

TABLE 7-continued

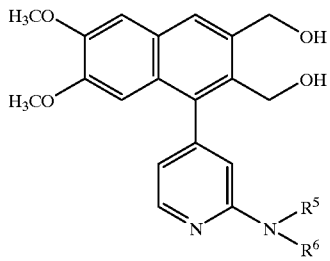

| Ex. No. | —NR⁵R⁶ | Physical properties |
|---|---|---|
| 88 | 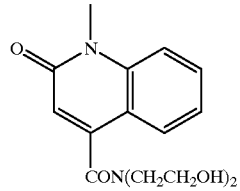　CON(CH₂CH₂OH)₂ | M.p. 65–68° C. |

TABLE 7-continued

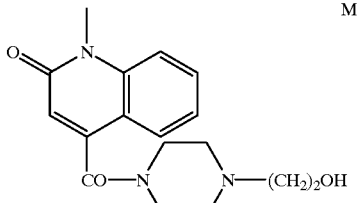

| Ex. No. | —NR⁵R⁶ | Physical properties |
|---|---|---|
| 89 | (1-methyl-2-oxoquinolin-4-yl)CO–N(piperazine)N–(CH₂)₂OH | M.p. 150–153° C. |

TABLE 8

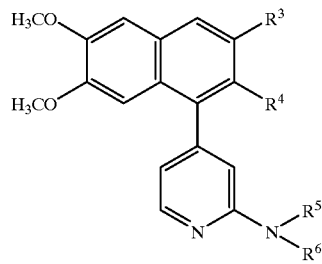

| Ex. No. | R³ | R⁴ | —NR⁵R⁶ | Physical properties |
|---|---|---|---|---|
| 90 | —CH₂OH | —CH₂OCOCH₂NH—COOC(CH₃)₃ | 1-methyl-2-oxoquinolin-4-yl | M.p. 120–122° C. |
| 91 | —CH₂OCOCH₂NH—COOC(CH₃)₃ | —CH₂OH | 1-methyl-2-oxoquinolin-4-yl | M.p. 136–138° C. |
| 92 | —CH₂OCOCH₂NH—COOC(CH₃)₃ | —CH₂OCOCH₂NH—COOC(CH₃)₃ | 1-methyl-2-oxoquinolin-4-yl | Oily product |

TABLE 8-continued
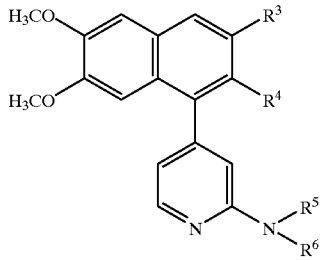
| Ex. No. | R³ | R⁴ | —NR⁵R⁶ | Physical properties |
|---|---|---|---|---|
| 93* | —CH₂OCOCH₂NH₂ | —CH₂OH | 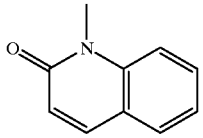 | M.p. 126–128° C. (decomposed) |
| 94* | —CH₂OH | —CH₂OCOCH₂NH₂ | 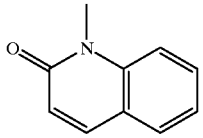 | M.p. 146–149° C. (decomposed) |
| 95** | —CH₂OCOCH₂NH₂ | —CH₂OCOCH₂NH₂ | 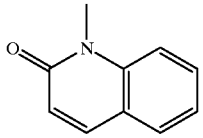 | M.p. 165–168° C. (decomposed) |
| 96 | —CH₂OH | —CH₂OCH₂COOC₂H₅ | 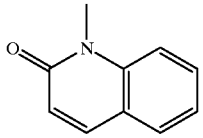 | M.p. 190–192° C. |
| 97 | —CH₂OCH₂COOC₂H₅ | —CH₂OH | 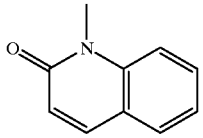 | M.p. 124–126° C. |
| 98 | —CH₂OCH₂CO—N(piperazine)N—CH₃ | —CH₂OH | 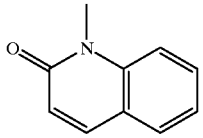 | M.p. 100–102° C. |
| 99** | —CH₂OH | —CH₂OH | 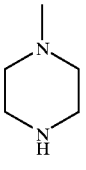 | M.p. >250° C. |
*Hydrochloride
**Dihydrochloride

TABLE 9
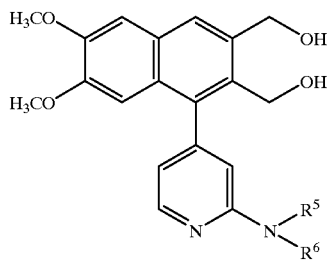
| Ex. No. | —NR⁵R⁶ | Physical properties |
|---|---|---|
| 100* | 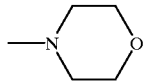 | M.p. 231–232° C. (decomposed) |
| 101* | 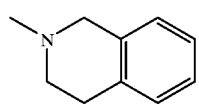 | M.p. 200–203° C. (decomposed) |
TABLE 9-continued
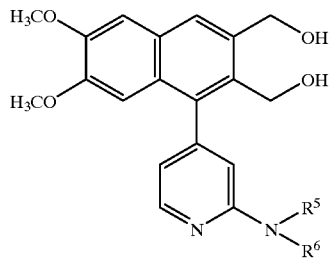
| Ex. No. | —NR⁵R⁶ | Physical properties |
|---|---|---|
| 102 | 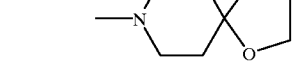 | M.p. 100–103° C. |
| 103* | | M.p. >250° C. |
*Hydrochloride
TABLE 10
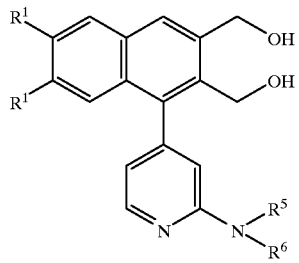
| Ex. No. | R¹ | R² | —NR⁵R⁶ | Physical properties |
|---|---|---|---|---|
| 104* | —OCH₃ | —OC₂H₅ | 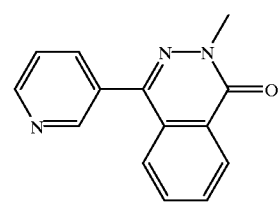 | M.p. 211–215° C. (decomposed) |
| 105* | —OC₂H₅ | —OC₂H₅ | 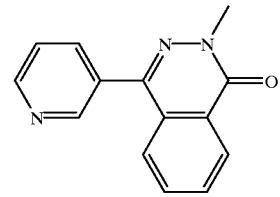 | M.p. 207–211° C. (decomposed) |

TABLE 10-continued

| Ex. No. | R¹ | R² | —NR⁵R⁶ | Physical properties |
|---|---|---|---|---|
| 106* | —OCH₃ | —OCH₃ | (2-methyl-1-oxo-phthalazin-4-yl)-4-(N,N-dimethylamino)phenyl group | M.p. 200–202° C. (decomposed) |
| 107* | —OCH₃ | —OCH₃ | 2-methyl-6,7-dimethoxy-4-(pyridin-3-yl)phthalazin-1(2H)-one group | M.p. 252–255° C. (decomposed) |
| 108 | —OCH₃ | —OCH₃ | 2-methyl-4-hydroxyphthalazin-1(2H)-one group | M.p. >250° C. |
| 109 | —OCH₃ | —OCH₃ | —NHNHCOCH₃ | M.p. 154–156° C. |

*Hydrochloride

TABLE 11
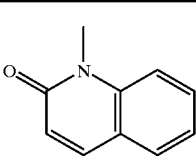
| Ex. No. | R³ | R⁴ | —NR⁵R⁶ | Physical properties |
|---|---|---|---|---|
| 110 | —CH₃ | —CH₂OH | 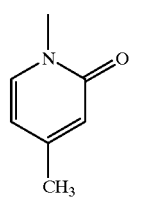 | M.p. 235–238° C. |
| 111 | —CH₃ | —CH₂OH | 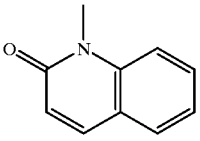 | M.p. 189–190° C. |
| 112 | H | —CH₂OH | 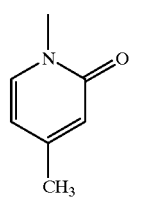 | M.p. 224–226° C. |
| 113 | H | —CH₂OH | 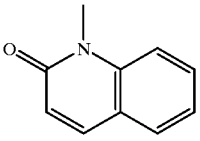 | M.p. 117–120° C. |
| 114* | H | —CH₂OH | 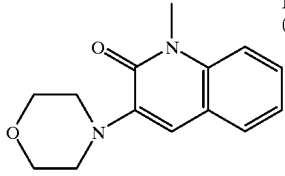 | M.p.181–183° C. (decomposed) |
*Hydrochloride

TABLE 12

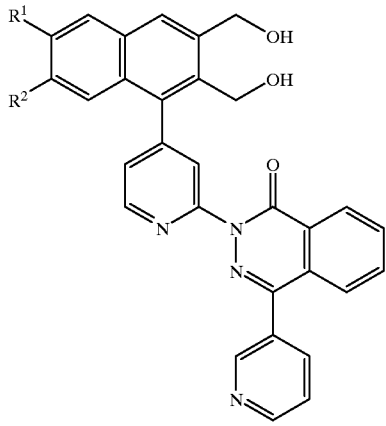

| Ex. No. | R¹ | R² | Physical properties |
|---|---|---|---|
| 115* | 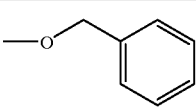 | —OCH₃ | M.p. 219–221° C. (decomposed) |
| 116* | —OH | —OCH₃ | M.p. >270° C. |
| 117* |  | —OCH₃ | M.p. 215–217° C. (decomposed) |
| 118* | —OCH(CH₃)₂ | —OCH₃ | M.p. 203–206° C. (decomposed) |
| 119* | —O(CH₂)₃CH₃ | —OCH₃ | M.p. 198–201° C. (decomposed) |
| 120* | —O(CH₂)₇CH₃ | —OCH₃ | M.p. 190–193° C. (decomposed) |
| 121 | —OCH₃ | —OCH₃ | M.p. 269–270° C. |
| 122 | —OC₂H₅ | —OC₂H₅ | M.p. 222° C. |
| 123*** | —OC₂H₅ | —OC₂H₅ | M.p. 141° C. |

*Hydrochloride
***Dihydrate

TABLE 13

| Ex. No. | R¹ | R² | R³ | R⁴ | Physical properties |
|---|---|---|---|---|---|
| 124* | —OCH₃ | —OCH₃ | —CH₂OH | H | M.p. >250° C. |

*Hydrochloride

TABLE 14

| Ex. No. | —NR⁵R⁶ | Physical properties |
|---|---|---|
| 125* | 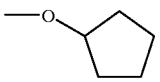 | M.p. 197–201° C. (decomposed) |
| 126 |  | M.p. 203–204° C. |
| 127 | 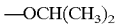 | M.p. 223–225° C. |
| 128 |  | M.p. 220–221° C. |

*Hydrochloride

EXAMPLE 1

A suspension of 1-(4-pyridyl)-2,3-bis(acetoxymethyl)-6,7-diethoxy) naphthalene N-oxide (3.5 g) and 1-chloroisoquinoline (1.26 g) in mesitylene (30 ml) is heated with stirring at 150–160° C. After the reaction is complete, the mixture is concentrated under reduced pressure to remove the solvent, and ethylene chloride and an aqueous sodium hydrogen carbonate solution are added to the resulting residue. The methylene chloride layer is separated, washed, dried, and concentrated under reduced pressure to remove the solvent. The reside is purified by silica gel column chromatography (solvent; chloroform:acetone= 30:1) to give 1-[2-(1-oxo-1,2-dihydroisoquinolin-2-yl)-4-- pyridyl]-2,3-bis(acetoxymethyl)-6,7-diethoxynaphthalene (1.85 g) which is listed in Table 1.

M.p. 90–93° C.

EXAMPLE 2

To a suspension of 1-(4-pyridyl)-2,3-bis(acetoxymethyl)-6,7-dimethoxynaphthalene N-oxide (2.3 g) and 2-chloroquinoline (1.64 g) in dimethylformamide (5 ml) is poured several drops of a solution of hydrogen chloride in dioxane, and the mixture is heated with stirring at 120–130° C. After the reaction is complete, the mixture is concentrated under reduced pressure to remove the solvent, and methylene chloride and an aqueous sodium hydrogen carbonate solution are added to the resulting residue. The methylene chloride layer is separated, washed, dried, and concentrated under reduced pressure to remove the solvent. To the residue are added pyridine (5 ml) and acetic anhydride (1.0 ml) under ice-cooling, an d t he mixture is stirred at room temperature for two hours. After the reaction is complete, the mixture is concentrated under reduced pressure to remove the solvent, and to the residue are added ethyl ace:ate and water. The ethyl acetate layer is separated, washed, dried and concentrated under reduced pressure. The residue is purified by silica gel column chromatography (solvent; chloroform:acetone=5:1) to give 1-[2-(2-oxo-1,2-dihydroquinolin-1-yl)-4-pyridyl]-2,3-bis(acetoxymethyl)-6,7-dimethoxynaphthalene (1.20 ,) which is listed in Table 1.

M.p. 181–184° C.

EXAMPLE 3

To a suspension of 1-(4-pyridyl)-2,3-bis(acetoxymethyl)-6,7-dimethoxynaphthalene N-oxide (3.5 g) and 2-chloro-5-nitropyridine (13.0 g) in xylene (30 ml) is added several drops of a solution of hydrogen bromide in acetic acid, and the mixture is heated with stirring at 140–150° C. After the reaction is complete, the mixture is concentrated under reduced pressure to remove the solvent, and chloroform and an aqueous sodium hydrogen carbonate solution are added to the resulting residue. The chloroform layer is separated, washed, dried, and concentrated under reduced pressure to remove the solvent. The residue is purified by silica gel column chromatography (solvent; chloroform:acetone=50:1) to give 1-{2-[2-oxo-1,2-dihydro-2-nitropyridin-1-yl]-4-pyridyl}-2,3-bis) (acetoxymethyl)-6,7-dimethoxynaphthalene (1.83 g) which is listed in Table 1.

M.p. 81–84° C.

EXAMPLE 4

To a solution of 1-[2-(1-oxo-1,2-dihydroisoquinolin-2-yl)-4-pyridyl]-2,3-bis(acetoxymethyl)-6,7-diethoxynaphthalene (1.84 g) in methanol (50 ml) is added sodium methoxide (0.52 g) under ice-cooling. The mixture is stirred at room temperature for 2.5 hours. To the mixture is added sodium methoxide (0.17 g) under ice-cooling, and the mixture is stirred at room temperature for one hour. Acetic acid (0.74 ml) is added to the reaction mixture under ice-cooling, and the mixture is Concentrated under reduced pressure to remove the solvent. To the residue are added methylene chloride and an aqueous sodium hydrogen carbonate solution, and the methylene chloride layer is separated, washed, dried and concentrated under reduced pressure to remove the solvent. The residue is purified by silica gel column chromatography (solvent; chloroform:ethanol=25:1) to give 1-[2-(1-oxo-1,2-dihydroisoquinolin-2-yl)4-pyridyl]-2,3-bis (hydroxymethyl)-6,7-diethoxynaphthalene (0.95 g) which is listed in Table 1.

M.p. 131–134° C.

EXAMPLE 5

To a solution of 1-{2-[2-oxo-1,2-dihydro-5-nitropyridin-1-yl]-4-pyridyl}-2,3-bis(acetoxymethyl)-6,7-dimethoxynaphthalene (1.83 g) in methanol (50 ml) is added sodium methoxide (0.72 g) under ice-cooling. The mixture is stirred at room temperature for one hour. To the mixture is added acetic acid (0.8 ml) under ice-cooling, and the mixture is concentrated under reduced pressure to remove the solvent. To the residue are added chloroform and an aqueous sodium hydrogen carbonate solution, and the chloroform layer is separated, washed, dried and concentrated under reduced pressure to remove the solvent. The residue is purified by silica gel column chromatography (solvent; chloroform:acetone=3:1), and crystallized from ethyl acetate to give 1-{2-[2-oxo-1,2-dihydro-5-nitropyridin-1-yl]-4-pyridyl}-2,3-bis(hydroxymethyl)-6,7-dimethoxynaphthalene (0.81 g,), which is listed in Table 1.

M.p. 248–251° C. (decomposed)

EXAMPLE 6

(1) To a suspension of 1-(2-bromo-4-pyridyl)-2,3-bis(methoxycarbonyl)-6,7-dimethoxynaphthalene (15.0 g) in tetrahydrofuran (150 ml) is added sodium borohydride (6.16 g), and the mixture is refluxed. To the mixture is added a mixture of methanol (60 ml) and tetrahydrofuran (60 ml) under reflux over a period of five hours. After the reaction is complete, the mixture is concentrated under reduced pressure to remove the solvent, and methyl chloride are an aqueous sodium hydrogen carbonate solution are added to the residue. The methylene chloride layer is separated, washed, dried and concentrated under reduced pressure to remove the solvent. The residue is crystallized from isopropyl ether to give 1-(2-bromo-4-pyridyl)-2,3-bis(hydroxymethyl)-6,7-dimethoxynaphthalene (11.86 g).

M.p. 177–17° C.

(2) A solution of 2-hydroxyquinoxaline (2.92 g) in dimethylformamide (20 ml) is cooled with ice under nitrogen atmosphere, and thereto is added 60 % sodium hydride (0.78 g). The mixture is stirred at room temperature for 15 minutes, and thereto is added copper (I) iodide (4.19 g). The mixture is stirred at 120° C. for 15 minutes, and cooled to room temperature. To the mixture is added 1-(2-bromo-4-pyridyl)-2,3-bis(hydroxymethyl)-6,7-dimethoxynaphthalene (2.02 g), and the mixture is stirred at 120° C. for five hours. After the reaction is complete, to the mixture are added ethyl acetate and aqueous ammonia, and the ethyl acetate layer is collected. The ethyl acetate layer is filtered, washed, dried, and concentrated under reduced pressure to remove the solvent. The residue is purified by silica gel column chromatography (solvent; chloroform:methanol=20:1) to give 1-[2-(2-oxo-1,2-dihydroquinoxalin-1-yl)-4-pyridyl]-2,3-bis(hydroxymethyl)-6,7-dimethoxynaphthalene (450 mg), which is listed in Table 2.

M.p. 158–165° C. (decomposed)

EXAMPLE 7

A solution of 2-hydroxy-4-[2-(1-piperidino)ethyl]aminoquinoline (3.26 g) in dimethylformamide (10 ml) is cooled with ice under nitrogen atmosphere. To the mixture is added 60 % sodium hydride (0.48 g), and the mixture is stirred at room temperature for 15 minutes. To the mixture is added copper (I) iodide (2.29 g), and the mixture is stirred at 120° C. for 30 minutes. The mixture is cooled to room temperature, and thereto is added 1-(2-bromo-4-pyridyl)-2,3-bis(hydroxymethyl)-6,7-dimethoxynaphthalene (2.43 g), and the mixture is stirred at 120° C. for five hours. After the reaction is complete, to the mixture are added ethyl acetate and aqueous ammonia, and the ethyl acetate layer is collected. The ethyl acetate layer is filtered, washed, dried, and concentrated under reduced pressure to remove the solvent. The residue is purified by silica gel column chromatography (solvent; chloroform:methanol=6:1), and thereto is added several-drops of a solution of hydrogen chloride in dioxane to crystallize. The precipitated crystals are washed, and dried to give 1-{2-[2-oxo-4-[2-(1-piperidino)ethyl]amino-1,2-dihydroquinolin-1-yl]-4-pyridyl}-2,3-bis(hydroxymethyl)-6,7-dimethoxynaphthalene hydrochloride (210 mg), which is listed in Table 2.

M.p. >220° C.

EXAMPLES 8–57

1-(2-Bromo-4-pyridyl)-2,3-bis(hydroxymethyl)-6,7-dimethoxy-naphthalene and the corresponding nitrogen-containing compounds [III] are treated in the same manner as in Example 6-(2) or Example 7 to give the compounds as listed in Table 2.

EXAMPLE 58

(1) 1-(2-Bromo-4-pyridyl)-2,3-bis(methoxycarbonyl)-6-ethoxy-7-methoxynaphthalene is treated in the same manner as in Example 6-(1) to give 1-(2-bromo-4-pyridyl)-2,3-bis(hydroxymethyl)-6-ethoxy-7-methoxynaphthalene.

M.p. 156–157° C.

(2) The above product and the corresponding nitrogen-containing compound [III] are treated in the same manner as in Example 7 to give 1-[2-{4-(3-pyridyl)-1(2H)-phthalazinon-2-yl}pyridin-4-yl]-2,3-bis(hydroxymethyl)-6-ethoxy-7-methoxynaphthalene hydrochloride, which is listed in Table 3.

M.p. 215–218° C. (decomposed)

Sulfate:

M.p. >250° C.

Methanesulfonate:

M.p. 205–215° C. (decomposed)

EXAMPLES 59–60

(1) 1-(2-Bromo-4-pyridyl)-2,3-bis(methoxycarbonyl)naphthalene is treated in the same manner as in Example 6-(1) to give 1-(2-bromo-4-pyridyl)-2,3-bis(hydroxymethyl)naphthalene.

M.p. 108–109° C.

(2) The above product and the corresponding nitrogen-containing compounds [III] are treated in the same manner as in Example 6-(2) or Example 7 to give the compounds as listed in Table 3.

EXAMPLES 61–62

(1) 1-(2-Bromo-5-pyridyl)-2,3-bis(methoxycarbonyl)-6,7-dimethoxynaphthalene is treated in the same manner as in Example 6-(1) to give 1-(2-bromo-5-pyridyl)-2,3-bis(hydroxymethyl)-6,7-dimethoxynaphthalene.

M.p. 185–186° C. (decomposed)

(2) The above product and the corresponding nitrogen-containing compounds [III] are treated in the same manner as in Example 6-(2) or Example 7 to give the compounds as listed in Table 4.

EXAMPLE 63

(1) To a suspension of 1-(2-bromo-6-pyridyl)-2,3-bis(methoxycarbonyl)-6,7-dimethoxynaphthalene (715 mg) in tetrahydrofuran (20 ml) is added lithium borohydride (174 mg), and the mixture is refluxed. To the mixture is added dropwise a mixture of methanol (2.2 ml) and tetrahydrofuran (10 ml) under reflux over a period of two hours. After the reaction is complete, the mixture is concentrated under reduced pressure to remove the solvent, and ethyl acetate and water are added to the residue. The ethyl acetate layer is separated, washed, dried, and concentrated under reduced pressure to remove the solvent. The residue is purified by silica gel column chromatography (solvent; chloroform:methanol=15:1) to give 1-(2-bromo-6-pyridyl)-2,3-bis(hydroxymethyl)-6,7-dimethoxynaphthalene (505 mg).

M.p. 107–108° C.

(2) 1-(2-Bromo-6-pyridyl)-2,3-bis(hydroxymethyl)-6,7-dimethoxynaphthalene and the corresponding nitrogen-containing compound [III] are treated in the same manner as in Example 6-(2) to give 1-[2-(2-oxo-1,2-dihydroquinolin-1-yl)pyridin-6-yl]-2,3-bis(hydroxymethyl)-6,7-dimethoxynaphthalene, which is listed in Table 5.

M.p. 142–143° C.

EXAMPLE 64

1-(2-Bromo-4-pyridyl)-2,3-bis(hydroxymethyl)-6,7-dimethoxynaphthalene and potassium phthalimide are treated in the same manner as in Example 6-(2) to give 1-(2-amino-4-pyridyl)-2,3-bis(hydroxymethyl)-6,7-dimethoxynaphthalene which is a hydrolysis product of 1-(2-phthalimide-4-pyridyl)-2,3-bis(hydroxymethyl)-6,7-dimethoxynaphthalene and listed in Table 6.

M.p. 99–103° C.

EXAMPLE 65

1-(2-Bromo-4-pyridyl)-2,3-bis(hydroxymethyl)-6,7-dimethoxynaphthalene and 2-oxobenzoxazolidine are treated in the same manner as Example 6-(2) to give 1-[2-(2-hydroxyphenyl)amino-4-pyridyl)-2,3-bis(hydroxymethyl1)-6,7-dimethoxynaphthalene which is a hydrolysis product of 1-[2-(2-oxobenzoxazolidin-3-yl)-4-pyridyl)-2,3-bis(hydroxymethyl)-6,7-dimethoxynaphthalene and listed in Table 6.

M.p. 90–93° C.

EXAMPLE 66

(1) To a suspension of 1-(4-pyridyl)-2,3-bis(methoxycarbonyl)-6,7-dimethoxynaphthalen, N-oxide (1.99 g) in toluene (10 ml) is added 2-chloroquinoline (3.27 g). To the mixture is added five drops of a 30 % solution of hydrogen bromide in acetic acid, and the mixture is refluxed for 15 hours. After the mixture is concentrated under reduced pressure to remove the solvent, water and methylene chloride are added to the residue. The pH value e of the mixture is adjusted to pH 8 with an aqueous sodium hydrogen carbonate solution. The mixture is extracted with methylene chloride, and the extract is washed, dried and concentrated under reduced pressure to remove the solvent. The residue is purified by silica gel column chromatography (solvent; chloroform:acetone=4:1) to give 1-[2-(2-oxo-1,2-dihydroquinolin-1-yl)-4-pyridyl]-2,3-bis(methoxycarbonyl)-6,7-dimethoxynaphthalene (2.60 g).

M.p. >230° C.

(2) To a suspension of 1-[2-(2-oxo-1,2-dihydroquinolin-1-yl)-4-pyridyl]-2,3-bis(methoxycarbonyl)-6,7-dimethoxynaphthalene (200 mg) in tetrahydrofuran is added sodium borohydride (36 mg), and the mixture is refluxed. To the mixture is added methanol (0.3 ml) under reflux over a period of one hour. The mixture is cooled to room temperature, and thereto is added sodium borohydride (36 mg). To the mixture is added methanol (0.3 ml) under reflux over a period of one hour. After the reaction is complete, methylene chloride and diluted hydrochloric acid are added to the mixture. The methylene chloride layer is separated, washed, dried and concentrated under reduced pressure to remove the solvent. The residue is purified by silica gel column chromatography (solvent; chloroform:methanol= 20:1) to give 1-[2-(2-oxo-1,2-dihydroquinolin-1-yl)-4-pyridyl]-2,3-bis(hydroxymethyl)-6,7-dimethoxynaphthalene (90 mg), which is listed in Table 6.

M.p. >230° C. (recrystallized from ethyl acetate)

EXAMPLE 67

(1) 1-(4-Pyridyl)-2,3-bis(methoxycarbonyl)-6,7-dimethoxynaphthalene N-oxide and 4-[3-(1-imidazolyl) propyl]amino-2-chloroquinoline are treated in the same manner as in Example 66-(1) to give 1-{2-[2-oxo-4-[3-(1-imidazolyl)-propyl]amino-1,2-dihydroquinolin-1-yl]-4-pyridyl}-2,3-bis(methoxycarbonyl)-6,7-dimethoxynaphthalene which is listed in Table 15.

M.p. 142–148° C.

(2) To a suspension of the above product (2.2 g) in tetrahydrofuran is added sodium borohydride (640 mg), and the mixture is refluxed. To the mixture is added dropwise a mixture of methanol (5.4 ml) and tetrahydrofuran (6 ml) under reflux over a period of two hours. The mixture is cooled to room temperature, and thereto is added sodium borohydride (400 mg). To the mixture is added dropwise methanol (3.4 ml) under reflux over a period of 0.5 hour. After the reaction is complete, an aqueous sodium hydroxide solution and methylene chloride are added to the mixture under ice-cooling. The methylene chloride layer is separated, washed, dried and concentrated under reduced pressure to remove the solvent. The residue is purified by silica gel column chromatography (solvent; chloroform::methanol 2:1), and the resultant is dissolved in dioxane/ methanol, and crystallized with adding thereto a solution of hydrogen chloride in dioxane (0.29 ml). The crystals are collected, washed, and dried to give 1-{2-[2-oxo-4-[3-(1-imidazolyl)propyl]amino-1,2-dihydroquinolin-1-yl]-4-pyridyl)-2,3-bis(hydroxymethyl)-6,7-dimethoxynaphthalene hydrochloride (90 mg), which is listed in Table 6.

M.p. >220° C.

EXAMPLE 68–72

(1) 1-(4-Pyridyl)-2,3-bis(methoxycarbonyl)-6,7-dimethoxy (or diethoxy)-naphthalene N-oxide and the corresponding halogeno-nitrogen-containing compounds [V] are treated in the same manner as in Example 66-(1) to give the compounds as listed in Table 15.

TABLE 15

[Structure: naphthalene with R¹, R² substituents, COOCH₃ groups at 2,3-positions, and a pyridyl group with NR⁵R⁶ substituent]

| Ex. No. | R¹ | R² | —NR⁵R⁶ | Physical properties |
|---------|-----|-----|---------|---------------------|
| 67-(1) | —OCH₃ | —OCH₃ | [2-oxo-1,2-dihydroquinolin-1-yl with 4-NH(CH₂)₃-imidazolyl substituent] | M.p. 142–148° C. |
| 68-(1) | —OC₂H₅ | —OC₂H₅ | [2-oxo-1,2-dihydroquinolin-1-yl with 4-CH₃ substituent] | M.p. 95–98° C. |

TABLE 15-continued

[Structure: naphthalene with R¹, R² substituents, COOCH₃ groups at 2,3 positions, and a pyridyl group at position 1 with NR⁵R⁶ substituent]

| Ex. No. | R¹ | R² | —NR⁵R⁶ | Physical properties |
|---|---|---|---|---|
| 69-(1) | —OCH₃ | —OCH₃ | [1-methyl-2-oxo-1,2-dihydroquinolin-4-yl with NH(CH₂)₂-morpholine substituent] | M.p. 136–138° C. |
| 70-(1) | —OCH₃ | —OCH₃ | [1-methyl-2-oxo-1,2-dihydropyridin-4-yl] | M.p. 206–210° C. |
| 71-(1) | —OC₂H₅ | —OC₂H₅ | [1-methyl-2-oxo-1,2-dihydroquinolin-4-yl] | M.p. 214–217° C. |
| 72-(1) | —OC₂H₅ | —OC₂H₅ | [1-methyl-4-methyl-2-oxo-1,2-dihydropyridin-4-yl] | M.p. 135–138° C. |

(2) The compounds obtained in the above (1) are treated in the same manner as in Example 66-(2) to give the compounds as listed in Table 6.

EXAMPLE 73

(1) 1-(4-Pyridyl)-2,3-bis(methoxycarbonyl)-6,7-dimethoxynaphthalene N-oxide and 2-chloro-4-benzyloxycarbonylmethoxyquinoline are treated in the same manner as in Example 66-(1) to give 1-[2-(2-oxo-4-benzyloxycarbonylmethoxy-1,2-dihydroquinolin-1-yl)-4-pyridyl]-2,3-bis(methoxycarbonyl)-6,7-dimethoxynaphthalene.

M.p. 186–189° C.

(2) The compound obtained in the above (1) is treated in the same manner as in Example 66-(2) to give 1-{2-[2-oxo-4-(2-hydroxyethoxy)-1,2-dihydroquinolin-1-yl]-4-pyridyl}-2,3-bis(hydroxymethyl)-6,7-dimethoxynaphthalene which is listed in Table 6.

M.p. 100–110° C. (decomposed)

EXAMPLE 74

(1) 1-(4-Pyridyl)-2,3-bis(methoxycarbonyl)-6,7-dimethoxynaphthalene N-oxide and 2-chloro-4-morpholinocarbonylquinoline are treated in the same manner as in Example 66-(1) to give 1-[2-(2-oxo-4-morpholinocarbonyl-1,2-dihydroquinolin-1-yl)-4-pyridyl]-2,3-bis(methoxycarbonyl)-6,7-dimethoxynaphthalene.

M.p. 247–249° C.

(2) The compound obtained in the above (1) is treated in the same manner as in Example 66-(2) to give 1-(2-[2-(1-hydroxymethyl-3-hydroxypropyl)phenylamino]-4-pyridyl}-2,3-bis(hydroxymethyl)-6,7-dimethoxynaphthalene which is listed in Table 6.

M.p. 204–207° C.

EXAMPLE 75–81

(1) 1-(2-Bromo-4-pyridyl)-2,3-bis(methoxycarbonyl)-6,7-dimethoxynaphthalene and the corresponding nitrogen-containing, compounds (III) are in the same manner as in Example 6-(2) to give the compounds as listed in Table 16.

TABLE 16

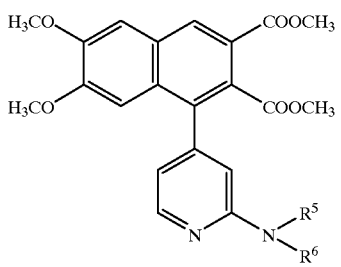

| Ex. No. | —NR⁵R⁶ | Physical properties |
|---|---|---|
| 75-(1) | [structure: N-methyl-2-oxo-4-(methoxymethoxy)quinoline] | M.p. 176–179° C. |
| 76-(1) | [structure: N-methyl-2-oxo-4-methoxyquinoline] | M.p. 123–126° C. (decomposed) |
| 77-(1) | [structure: 1,6-dimethyl-2-oxopyridine] | M.p. 72–75° C. |
| 78-(1) | [structure: 1-methyl-3-methyl-2-oxopyridine] | M.p. 181–184° C. |
| 79-(1) | [structure: 1,5-dimethyl-2-oxopyridine] | M.p. 206–209° C. |
| 80-(1) | [structure: N-methyl-2-oxo-5,6,7,8-tetrahydroquinoline] | M.p. 71–73° C. |
| 81-(1) | [structure: 2-methyl-3-oxoisoquinoline] | M.p. 81–84° C. |

(2) The compounds as listed in the above (1) are treated in the same manner as in Example 66-(2) to give the compounds as listed in Tables 6 and 7.

EXAMPLE 82

(1) 1-(2-Bromo-4-pyridyl)-2,3-bis(methoxycarbonyl)-6,7-dimethoxynaphthalene and 4-hydroxyquinoline are treated in the same manner as in Example 6-(2) to give 1-[2-(4-oxo-1,4-dihydroquinolin-1-yl)-4-pyridyl]-2,3-bis (methoxycarbonyl)-6,7-dimethoxynaphthalene.

M.p. 264–66° C. (decomposed) (2) The compound obtained in the above (1) is treated in the same manner as in Example 66-(2) to give 1-[2-(4-hydroxy-1,2,3,4-tetrahydroquinolin-1-yl)-4-pyridyl]-2,3-bis (hydroxymethyl)-6,7-dimethoxynaphthalene which is listed in Table 7.

M.p. 90–94° C.

EXAMPLE 83

(1) 1-(2-Bromo-4-pyridyl)-2,3-bis(methoxycarbonyl)-6,7-dimethoxynaphthalene and 5-methyl-2-oxopyrrolidine are treated in the same manner as in Example 6-(2) to give 1-[2-(5-methyl-2-oxopyrrolidin-1-yl)-4-pyridyl]-2,3-bis (methoxycarbonyl)-6,7-dimethoxynaphthalene.

M.p. 184–186° C.

(2) The compound obtained in the above (1) is treated in the same manner as in Example 66-(2) to give 1-[2-(1-methyl-4-hydroxybutyl)amino-4-pyridyl]-2,3-bis(hydroxymethyl)-6,7-dimethoxynaphthalene which is listed in Table 7.

M.p. 57–61° C.

EXAMPLE 84

(1) 1-(2-Bromo-4-pyridyl)-2,3-bis(methoxycarbonyl)-6,7-dimethoxynaphthalene and 2-oxo-1,2,3,4-tetrahydroquinoline are treated in the same manner as in Example 6-(2) to give 1-[2-(2-oxo-1,2,3,4-tetrahydroquinolin-1-yl)-4-pyridyl]-2,3-bis (methoxycarbonyl)-6,7-dimethoxynaphthalene.

M.p. 229–233° C.

(2) The compound obtained in the above (1) is treated in the same manner as in Example 66-(2) to give 1-{2-[2-(3-hydroxypropyl)phenyl]amino-4-pyridyl]-2,3-bis (hydroxymethyl)-6,7-dimethoxynaphthalene which is listed in Table 7.

M.p. 156–158° C.

EXAMPLE 85

1-[2-(2-Oxo-4-methoxymethoxy-1,2-dihydroquinolin-1-yl)-4-pyridyl]-2,3-bis(hydroxymethyl)-6,7-dimethoxynaphthalene (1.39 g) is dissolved in a mixture of dioxane (10 ml) and methanol (5 ml), and thereto is added 2M hydrochloric acid (2 ml). The mixture is warmed to 50° C., and stirred for 7 hours, and then concentrated under reduced pressure to remove the solvent. To the residue are added chloroform and water, and the chloroform layer is separated, washed, dried and concentrated under reduced pressure to remove the solvent. The residue is purified by silica gel column chromatography (solvent; chloroform:methanol=10:1) to give 1-[2-(2-oxo-4-hydroxy-1,2-dihydroquinolin-1-yl)-4-pyridyl]-2,3-bis (hydroxymethyl)-6,7-dimethoxy-naphthalene (0.79 g) which is listed in Table 7.

M.p. 160–170° C.

EXAMPLE 86

1-[2-(1-Oxo-5-methoxymethoxy-1,2-dihydroisoquinolin-2-yl)-4-pyridyl]-2,3-bis(hydroxymethyl)-6,7-dimethoxynaphthalene is treated in the same manner as in Example 85 to give 1-[2-(1-oxo-5-hydroxy-1,2-- dihydroquinolin-2-yl)-4-pyridyl]-2,3-bis(hydroxymethyl)-6,7-dimethoxynaphthalene, which is listed in Table 7.

M.p. 138–140° C.

EXAMPLE 87

1-[2-(2-Oxo-4-tert-butoxycarbonyl-1,2-dihydroquinolin-1-yl)-pyridyl]-2,3-bis(hydroxymethyl)-6,7-dimethoxynaphthalene (0.96 g) is added to a 4 M solution of hydrogen chloride in dioxane (25 ml) under ice-cooling, and the mixture is stirred at room temperature overnight. The mixture is concentrated under reduced pressure to remove the solvent, and the residue is purified by silica gel column chromatography (solvent; chloroform:methanol:acetic acid= 90:10:3), and crystallized from ethyl acetate to give 1-[2-(2-oxo-4-carboxy-1,2-dihydroquinolin-1-yl)-4-pyridyl]-2,3-bis(hydroxymethyl)-6,7-dimethoxynaphthalene (0.41 g) which is listed in Table 7.

M.p. >250° C.

EXAMPLE 88

To a solution of 1-{2-(2-oxo-4-bis(2-tert-butyldimethylsilyloxyethyl)aminocarbonyl-1,2-dihydroquinolin-1-yl]-4-pyridyl}-2,3-bis(hydroxymethyl)-6,7-dimethoxynaphthalene (1.9 g) in tetrahydrofuran (20 ml) is added a 1.0 M solution of tetrabutylammonium fluoride in tetrahydrofuran (2.8 ml) under ice-cooling, and the mixture is stirred at room temperature for one hour. After the reaction is complete, the mixture is concentrated under reduced pressure to remove the solvent, and to the resultant are added methylene chloride and an aqueous sodium hydrogen carbonate solution. The methylene chloride layer is separated, washed, dried, and concentrated under reduced pressure to remove the solvent. The residue is purified by silica gel column chromatography (solvent; chloroform:methanol=10:1~5:1), and triturated with ether to give 1-{2-(2-oxo-4-bis(2-hydroxyethyl)aminocarbonyl-1,2-dihydroquinolin-1-yl)-4-pyridyl}-2,3-bis(hydroxymethyl)-6,7-dimethoxynaphthalene (0.68 g) which is listed in Table 7.

M.p. 65–68° C.

EXAMPLE 89

1-{2-(2-Oxo-4-[4-(2-t-butyldimethylsilyloxyethyl) piperazin-1-yl]-carbonyl-1,2-dihydroquinolin-1-yl]-4-pyridyl}-2,3-bis(hydroxymethyl)-6,7-dimethoxynaphthalene is treated in the same manner as in Example 88 to give 1-{2-(2-oxo-4-[4-(2-hydroxyethyl) piperazin-1-yl]carbonyl-1,2-dihydroquinolin-1-yl]-4-pyridyl}-2,3-bis(hydroxymethyl)-6,7-dimethoxynaphthalene which is listed in Table 7.

M.p. 150–153° C.

EXAMPLE 90–92

A solution of 1-[2-(2-oxo-1,2-dihydroquinolin-1-yl)-4-pyridyl]-2,3-bis(hydroxymethyl,-6,7-dimethoxynaphthalene (3.1 g) in dimethylformamide (10 ml) is added with stirring to a solution of tert-butoxycarbonylglycine (2.1 g) and carbonyldiimidazole (2.14 g) in dimethylformamide (5 ml) over a period of 30 minutes, and the mixture is stirred at room temperature overnight. To the residue are added ethyl acetate and water, and the ethyl acetate layer is separated, washed, dried, and concentrated under reduced pressure to remove the solvent. The residue is purified by silica gel column chromatography (solvent; chloroform:methanol=20:1)1 to give 1-[2-(2-oxo-1,2-dihydroquinolin-1-yl)-4-pyridyl]-2-(t-butoxycarbonylaminomethylcarbonyloxymethyl)-3-hydroxymethyl- 6,7-dimethoxynaphthalene (0.8 g, Example 90), 1-[2-(2-oxo-1,2-dihydroquinolin-1-yl)-4-pyridyl]-2-hydroxymethyl-3-(t-butoxycarbonylaminomethylcarbonyloxymethyl)-6,7-dimethoxynaphthalene (1.2 g, Example 91) and 1-[2-(2-oxo-1,2-dihydroquinolin-1-yl)-4-pyridyl]-2,3-bis(t-butoxycarbonylaminomethylcarbonyloxymethyl)-6,7-dimethoxynaphthalene (0.47 g, Example 92), which are listed in Table 8.

(Example 90) M.p. 120–122° C.
(Example 91) M.p. 136–138° C.
(Example 92) Oily product

EXAMPLE 93

1-[2-(2-Oxo)-1,2-dihydroquinolin-1-yl)-4-pyridyl]-2-hydroxymethyl-3-(t-butoxycarbonylaminomethylcarbonyloxymethyl)-6,7-dimethoxynaphthalene (700 mg) is dissolved in trifluoroacetic acid (5 ml), and the mixture is stirred at room temperature for one hour. After the reaction is complete, the mixture is concentrated under reduced pressure to remove the solvent, and thereto are added methanol and a 15 % solution of hydrogen chloride in methanol (20 ml). The mixture is concentrated under reduced pressure to remove the solvent, and the residue is triturated with ether to give 1-[2-(2-oxo-1,2-dihydroquinolin-1-yl)-4-pyridyl]-2-hydroxymethyl-3-aminomethylcarbonyloxymethyl-6,7-dimethoxynaphthalene hydrochloride (510 mg), which is listed in Table 8.

M.p. 126–123° C. (decomposed)

EXAMPLE 94

1-[2-(2-Oxo-1,2-dihydroquinolin-1-yl)-4-pyridyl]-2-(t-butoxycarbonylaminomethylcarbonyloxymethyl)-3–1hydroxymethyl-6,7-dimethoxynaphthalene is treated in the same manner as in Example 93 to give 1-[2-(2-oxo-1, 2-dihydroquinolin- 1-yl)-4-pyridyl]-2-aminomethylcarbonyloxymethyl-3-hydroxymethyl-6,7-dimethoxynaphthalene hydrochloride which is listed in Table 8.

M.p. 146–149° C. (decomposed)

EXAMPLE 95

1-[2-(2-Oxo-1,2-dihydroquinolin-1-yl)-4-pyridyl]-2,3-bis (t-butoxycarbonylaminomethylcarbonyloxymethyl)-6,7-dimethoxynaphthalene is treated in the same manner as in Example 93 to give 1-[2-(2-oxo-1,2-dihydroquinolin-1-yl)-4-pyridyl]-2,3-bis(aminomethylcarbonyloxymethyl)-6,7-dimethoxynaphthalene dihydrochloride which is listed in Table 8.

M.p. 165–168° C. (decomposed)

EXAMPLES 96–97

To a solution of 1-[2-(2-oxo-1,2-dihydroquinolin-1-yl)-4-pyridyl]-2,3-bis(hydroxymethyl)-6,7-dimethoxynaphthalene (468 mg) in dimethylformamide (5 ml) is added sodium hydride (60 mg), and the mixture is stirred for 30 minutes. The mixture is cooled with ice, and thereto is added dropwise ethyl bromo-acetate (0.17 ml), and the mixture is stirred overnight. To the residue are added ethyl acetate and water, and the ethyl acetate layer is separated, washed, dried and concentrated under reduced pressure. The residue is purified by silica gel column chromatography (solvent; chloroform:acetone=5: 1) to give 1-[2-(2-oxo-1,2-dihydroquinolin-1-yl)-4-pyridyl]-2-ethoxycarbonylmethoxymethyl-3-hydroxymethyl-6,7-dimethoxynaphthalene (70 mg, Example 96) and 1-[2-(2-oxo-1,2-dihydroquinolin-1-yl)-4-pyridyl]-2-hydroxymethyl-3-ethoxycarbonylmethoxymethyl-6,7-dimethoxynaphthalene (120 mg, Example 97), which are listed in Table 8.

(Example 96) M.p. 190–192° C.

(Example 97) M.p. 124–126° C.

EXAMPLE 98

To a solution of 1-[2-(2-oxo-1,2-dihydroquinolin-1-yl)-4-pyridyl]-2-hydroxymethyl-3-ethoxycarbonylmethoxymethyl-6,7-dimethoxynaphthalene (200 mg) in tetrahydrofuran (5 ml) is added a 1 M aqueous sodium hydroxide solution (0.36 ml), and the mixture is stirred. To the solution is added methanol (5 ml), and the mixture is refluxed for 20 minutes. The reaction mixture is cooled to room temperature, and thereto is added 1M hydrochloric acid (0.36 ml), by which the pH value of the mixture is adjusted to about pH 4. Chloroform is added to the reaction mixture, and the chloroform layer is separated, washed, dried, and concentrated under reduced pressure to remove the solvent. To the residue is added methylene chloride, and then further thereto are added dicyclohexyl-carbodiimide (83 mg) and 1-hydroxybenzotriazole (61 mg), and the mixture is stirred at room temperature for 30 minutes. To the mixture is added 1-methylpiperazine (50 mg), and the mixture is stirred overnight. The reaction mixture is washed with water, and concentrated under reduced pressure to remove the solvent, and purified by silica gel column chromatography (solvent; chloroform:methanol=10:1) to give 1-[2-(2-oxo-1,2-dihydroquinolin-1-yl)-4-pyridyl]-2-hydroxymethyl-3-(4-methylpiperazin-1-yl)carbonylmethoxymethyl-6,7-dimethoxynaphthalene (150 mg), which is listed in Table 8.

M.p. 100–102° C.

EXAMPLE 99

(1) 1-(2-Chloro-4-pyridyl)-2,3-bis(methoxycarbonyl)-6,7-dimethoxynaphthalene is treated in the same manner as in Example 6-(1) to give 1-(2-chloro-4-pyridyl)-2,3-bis(hydroxymethyl)-6,7-dimethoxynaphthalene.

(2) A mixture of 1-(2-chloro-4-pyridyl)-2,3-bis(hydroxymethyl)-6,7-dimethoxynaphthalene (2.0 g) and piperazine is heated with stirring at 130° C. for 90 minutes. The mixture is cooled to room temperature, and thereto are added methylene chloride and water after the reaction is complete. The methylene chloride layer is separated, and concentrated under reduced pressure. The residue is dissolved in ethanol, and thereto is added a 4M solution of hydrogen chloride in dioxane (2.8 ml) to give a hydrochloride. The mixture is concentrated under reduced pressure to remove the solvent, and crystallized from ethanol to give 1-[2-(1-piperazinyl)-4-pyridyl]-2,3-bis(hydroxymethyl)-6,7-dimethoxynaphthalene dihydrochloride (1.57 g).

M.p. >250° C.

EXAMPLES 100–101

1-(2-Chloro-4-pyridyl)-2,3-bis(hydroxymethyl)-6,7-dimethoxynaphthalene and the corresponding nitrogen-containing compounds [III] are treated in the same manner as in Example 99-(2) to give the compounds as listed in Table 9.

EXAMPLE 102

A mixture of 1-(2-chloro-4-pyridyl)-2,3-bis(hydroxymethyl)-6,7-dimethoxynaphthalene (1.80 g) and 1,4-dioxa-8-azaspiro[4,5]decane is stirred at 140° C. for 18 hours. The mixture is cooled to room temperature, and thereto are added chloroform and water. The chloroform layer is separated, and concentrated under reduced pressure to remove the solvent. The residue is purified by silica gel column chromatography (solvent; chloroform:acetone=5:1) to give 1-[{2-(1,4-dioxa-8-azasprio[4,5]dec-8-yl)pyridin-4-yl]-2,3-bis(hydroxymethyl)-6,7-dimethoxynaphthalene (1.54 g, yield; 62%), which is listed in Table 9.

M.p. 100–103° C.

EXAMPLE 103

A mixture of 1-[2-(1,4-dioxa-8-azasprio[4,5]dec-8-yl)pyridin-4-yl]-2,3-bis(hydroxymethyl)-6,7-dimethoxynaphthalene (1.40 g), 70% perchloric acid (3.62 ml), tetrahydrofuran (15 ml) and water (10 ml) is stirred at room temperature for three days. After the reaction is complete, to the mixture are added chloroform and water. The chloroform layer is separated, and concentrated under reduced pressure to remove the solvent. The residue is purified by silica gel column chromatography (solvent; chloroform:acetone=2:1), and the resultant is dissolved in chloroform. To the mixture is added a 4M solution of hydrogen chloride in dioxane, and the mixture is concentrated under reduced pressure to remove the solvent to give 1-[2-(4-oxo-1-piperidinyl)-4-pyridyl]-2,3-bis(hydroxymethyl)-6,7-dimethoxynaphthalene hydrochloride (828 mg), which is listed in Table 9.

M.p. >250° C.

EXAMPLE 104

(1) 1-(2-Chloro-4-pyridyl)-2,3-bis(methoxycarbonyl)-6-methoxy-7-ethoxynaphthalene is treated in the same manner as in Example 6-(1) to give 1-(2-chloro-4-pyridyl)-2,3-bis(hydroxymethyl)-6-methoxy-7-ethoxynaphthalene.

M.p. 123–126° C.

(2) A suspension of 1-(2-chloro-4-pyridyl)-2,3-bis(hydroxymethyl)-6-methoxy-7-ethoxynaphthalene (16.0 g) in hydrazine hydrate (50 ml) is refluxed for four hours. The mixture is cooled to room temperature, and then thereto is added water. The precipitated crystals are collected by filtration, washed with water, and dried to give 1-(2-hydrazino-4-pyridyl)-2,3-bis(hydroxymethyl)-6-methoxy-7-ethoxynaphthalene (14.5 g).

M.p. 197–200° C.

(3) A mixture of 1-(2-hydrazino-4-pyridyl)-2,3-bis(hydroxymethyl)-6-methoxy-7-ethoxynaphthalene (2.0 a), (2-carboxyphenyl)-(3-pyridyl) ketone (1.35 g) and ethylene glycol (5 ml) is refluxed for two hours. The mixture under refluxing is cooled to room temperature, and then thereto are added methylene chloride and water. The methylene chloride layer is separated, washed, dried, concentrated under reduced pressure to remove the solvent, and crystallized from chloroform. The precipitated crystals are dissolved in a mixture of chloroform and methanol, and thereto is added a 4 M solution of hydrogen chloride in dioxane (0.67 ml) to give 1-[2-{4-(3-pyridyl)-1(2H)-phthalazinon-2-yl}-4-pyridyl]-2,3-bis(hydroxymethyl)-6-methoxy-7-ethoxynaphthalene hydrochloride (1.43 g), which is listed in Table 10.

M.p. 211–21.5° C. (decomposed)

EXAMPLE 105

(1) 1-(2-Chloro-4-pyridyl)-2,3-bis(methoxycarbonyl)-6,7-diethoxynaphthalene is treated in the same manner as in Example 6-(1) to give 1-(2-chloro-4-pyridyl)-2,3-bis (hydroxymethyl)-6,7-diethoxynaphthalene.

M.p. 148–150° C.

(2) 1-(2-Chloro-4-pyridyl)-2,3-bis(hydroxymethyl)-6,7-diethoxynaphthalene is treated in the same manner as in Example 104-(2) to give 1-(2-hydrazino-4-pyridyl)-2,3-bis (hydroxymethyl)-6,7-diethoxynaphthalene.

M.p. 225–230° C. (decomposed)

(3) 1-(2-Hydrazino-4-pyridyl)-2,3-bis(hydroxymethyl)-6,7-diethoxynaphthalene is treated in the same manner in Example 104-(3) to give 1-[2-{4-(3-pyridyl)-1(2H)-phthalazinon-2-yl}-4-pyridyl]-2,3-bis(hydroxymethyl)-6,7-diethoxynaphthalene hydrochloride which is listed in Table 10.

M.p. 207–211° C. (decomposed)

EXAMPLES 106–107

(1) 1-(2-Bromo-4-pyridyl)-2,3-bis(hydroxymethyl)-6,7-dimethoxy-naphthalene is treated in the same manner as in Example 104-(2) to give 1-(2-hydrazino-4-pyridyl)-2,3-bis (hydroxymethyl)-6,7-dimethoxynaphthalene.

M.p. 214–220° C.

(2) 1-(2-Hydrazino-4-pyridyl)-2,3-bis(hydroxymethyl)-6,7-dimethoxynaphthalene and the corresponding carboxylic acid derivative [VII] are treated in the same manner as in Example 104-(3) to give the compounds as listed in Table 10.

EXAMPLE 108

A mixture of 1-(2-hydrazino-4-pyridyl)-2,3-bis (hydroxymethyl)-6,7-dimethoxynaphthalene (2.0 g), phthalic anhydride (0.92 g) and ethylene glycol (10 ml) is heated with stirring at 130° C. for two hours. The mixture is cooled to room temperature, and thereto are added methylene chloride and water. The methylene chloride layer is separated, washed, dried, concentrated under reduced pressure to remove the solvent, and the residue is crystallized from ethanol to give 1-[2-{4-(hydroxy)-1(2H)-phthalazinon-2-yl}-4-pyridyl]-2,3-bis(hydroxymethyl)-6,7-dimethoxynaphthalene (1.68 g, yield; 61%), which is listed in Table 10.

M.p. >250° C.

EXAMPLE 109

A mixture of 1-(2-hydrazino-4-pyridyl)-2,3-bis (hydroxymethyl)-6,7-dimethoxynaphthalene (2.0 g) and acetic acid (20 ml) is stirred at room temperature for 96 hours. After the reaction is complete, to the mixture are added methylene chloride and an aqueous potassium carbonate solution. The methylene chloride layer is separated, concentrated under reduced pressure, and the residue is crystallized from chloroform to give 1-[2-(2-acetylhydrazino)-pyridin-4-yl]-2,3-bis(hydroxymethyl)-6,7-dimethoxynaphthalene (0.84 g), which is listed in Table 10.

M.p. 154–1.56° C.

EXAMPLES 110–111

(1) 1-(2-Bromo-4-pyridyl)-2-methoxycarbonyl-3-methyl-6,7-dimethoxynaphthalene is treated in the same manner as in Example 6-(1) to give 1-(2-bromo-4-pyridyl)-2-hydroxymethyl-3-methyl-6,7-dimethoxynaphthalene.

M.p. 106–108° C.

(2) The above compound and the corresponding nitrogen-containing compounds [III] are treated in the same manner as in Example 6-(2) to give the compounds as listed in Table 11.

EXAMPLES 112–114

(1) 1-(2-Bromo-4-pyridyl)-2-methoxycarbonyl-6,7-dimethoxynaphthalene is treated in the same manner as in Example 6-(1) to give 1-(2-bromo-4-pyridyl)-2-hydroxymethyl-6,7-dimethoxynaphthalene.

M.p. 150–153° C.

(2) The above compound and the corresponding nitrogen-containing compounds [III] are treated in the same manner as in Example 6-(2) or Example 7 to give the compounds as listed in Table 11.

EXAMPLE 115

(1) 1-(2-Chloro-4-pyridyl)-2,3-bis(methoxycarbonyl)-6-benzyloxy-7-methoxynaphthalene is treated in the same manner as in Example 6-(1) to give 1-(2-chloro-4-pyridyl)-2,3-bis(hydroxymethyl)-6-benzyloxy-7-methoxynaphthalene.

M.p. 215–217° C. (decomposed)

(2) 1-(2-Chloro-4-pyridyl)-2,3-bis(hydroxymethyl)-6-benzyloxy-7-methoxynaphthalene is treated in the same manner as in Example 104-(2) to give 1-(2-hydrazino-4-pyridyl)-2,3-bis(hydroxymethyl)-6-benzyloxy-7-methoxynaphthalene.

M.p. 155–157° C.

(3) 1-(2-Hydrazino-4-pyridyl)-2,3-bis(hydroxymethyl)-6-benzyloxy-7-methoxynaphthalene is treated in the same manner as in Example 104-(3) to give 1-[2-{4-(3-pyridyl)-1(2H)-phthalazinon-2-yl}-4-pyridyl]-2,3-bis (hydroxymethyl)-6-benzyloxy-7-methoxynaphthalene hydrochloride, which is listed in Table 12.

M.p. 219–221° C. (decomposed)

EXAMPLE 116

To a solution of 1-[2-{4-(3-pyridyl)-1(2H)-phthalazinon-2-yl}-4-pyridyl]-2,3-bis(hydroxymethyl)-6-benzyloxy-7-methoxynaphthalene (0.73 g) in dichloromethane (10 ml) are added dropwise acetic anhydride (0.7 ml) and triethylamine (1.3 ml) under ice-cooling, and the mixture is stirred at room temperature overnight. The mixture is diluted with dichloromethane, washed with water, dried, and concentrated under reduced pressure to remove the solvent. The residue is dissolved in acetic acid (50 ml) and thereto is added 10% palladium-carbon (0.1 g), and the mixture is subjected to medium-pressure catalytic hydrogenation at room temperature overnight with using a Parr reduction apparatus;. The catalyst is removed by filtration, and the filtrate is concentrated under reduced pressure. The residue is dissolved in methanol (10 ml), and thereto is added sodium methoxide (0.2 g) under ice-cooling. The mixture is stirred at room temperature for three hours, and thereto is added diluted hydrochloric acid under ice-cooling. The mixture is concentrated under reduced pressure to remove the solvent. Water is added to the residue, and the mixture is extracted with dichloromethane. The extract is washed, dried, and concentrated under reduced pressure to remove the solvent. The residue is crystallized from ethyl acetate, and thereto is added 4M hydrogen chloride in ethyl acetate to give 1-[2-{4-(3-pyridyl)-1(2H)-phthalazinon-2-yl}-4-pyridyl]-2,3-bis(hydroxymethyl)-6-hydroxy-7-methoxynaphthalene hydrochloride (0.15 g, yield; 25%), which is listed in Table 12.

M.p. >270° C.

EXAMPLE 117

(1) To a suspension of 1-(2-chloro-4-pyridyl)-2,3-bis (methoxycarbonyl)-6-benzyloxy-7-methoxynaphthalene (6.6 g) in a mixture of acetic acid and dioxane (1:1, 1000 ml)

is added 10% palladium-carbon (2 g), and the mixture is subjected to medium-pressure catalytic hydrogenation at room temperature overnight with using, a Parr-reduction apparatus. To the reaction solution is added a mixture of acetic acid and dioxane (1000 ml), and thereto is added 10% palladium-carbon (2 g). The mixture is subjected to medium-pressure catalytic hydrogenation at room temperature for 18 hours with using a Parr-reduction apparatus. The catalyst is removed by filtration, and the filtrate is concentrated under reduced pressure. The residue is crystallized from ethanol to give 1-(2-chloro4-pyridyl)-2,2-bis (methoxycarbonyl)-6-hydroxy-7-methoxynaphthalene (3.35 g, yield; 62%).

M.p. 231–233° C. (decomposed)

(2) To a solution of 1-(2-chloro-4-pyridyl)-2,2-bis (methoxycarbonyl)-6-hydroxy-7-methoxynaphthalene (3.34 g) in dimethylformamide (150 ml) is added sodium hydride (0.4 g) under ice-cooling, and the mixture is stirred at room temperature for 30 minutes. To the reaction mixture is added dropwise cyclopentyl bromide (1.8 ml), and the mixture is heated with stirring at 80° C. overnight. The mixture is heated at 130° C. for two hours. To the resultant are added chloroform and water, and the chloroform layer is separated, washed, dried, and concentrated under reduced pressure to remove the solvent. The residue is crystallized from 1-(2-chloro-4-pyridyl)-2,3-bis(methoxycarbonyl)-6-cyclopentyloxy-7-methoxynaphthalene (1.24 g, yield; 32%).

M.p. 179–181° C.

(3) 1-(2-Chloro-4-pyridyl)-2,3-bis(methoxycarbonyl)-6-cyclopentyloxy-7-methoxynaphthalene is treated in the same manner as in Example 6-(1) to give 1-(2-chloro-4-pyridyl)-2,3-bis(hydroxymethyl)-6-cyclopentyloxy-7-methoxynaphthalene.

M.p. 200–201° C.

(4) 1-(2-Chloro-4-pyridyl)-2,3-bis(hydroxymethyl)-6-cyclopentyloxy-7-methoxynaphthalene is treated in the same manner as in Example 104-(2) to give 1-(2-hydrazino-4-pyridyl)-2,3-bis(hydroxymethyl)-6-cyclopentyloxy-7-methoxynaphthalene.

M.p. 127–130° C.

(5) 1-(2-Hydrazino-4-pyridyl)-2,3-bis(hydroxymethyl)-6-cyclopentyloxy-7-methoxynaphthalene is treated in the same manner as in Example 104-(3) to give 1-[2-{4-(3-pyridyl)-1(2H)-phthalazinon-2-yl}-4-pyridyl]-2,3-bis (hydroxymethyl)-6-cyclopentyloxy-7-methoxynaphthalene hydrochloride, which is listed in Table 12.

M.p. 215–217° C. (decomposed)

EXAMPLE 118

(1) 1-(2-Chloro-4-pyridyl)-2,3-bis(methoxycarbonyl)-6-isopropyloxy-7-methoxynaphthalene is treated in the same manner as in Example 6-(1) to give 1-(2-chloro-4-pyridyl)-2,3-bis(hydroxymethyl)-6-isopropyloxy-7-methoxynaphthalene.

M.p. 129–131° C.

(2) 1-(2-Chloro-4-pyridyl)-2,3-bis(hydroxymethyl)-6-isopropyloxy-7-methoxynaphthalene is treated in the same manner as in Example 104-(2) to give 1-(2-hydrazino-4-pyridyl)-2,3-bis(hydroxymethyl)-6-isopropyloxy-7-methoxynaphthalene.

M.p. 128–131° C.

(3) 1-(2-Hydrazino-4-pyridyl)-2,3-bis(hydroxymethyl)-6-isopropyloxy-7-methoxynaphthalene is treated in the same manner as in Example 104-(3) to give 1-[2-{4-(3-pyridyl)-1(2H)-phthalazinon-2-yl}-4-pyridyl]-2,3-bis(chydroxymethyl)-6-isopropyloxy-7-methoxynaphthalene hydrochloride, which is listed in Table 12.

M.p. 203–206° C. (decomposed)

EXAMPLE 119

(1) 1-(2-Chloro-4-pyridyl)-2,3-bis(methoxycarbonyl)-6-butoxy-7-methoxynaphthalene is treated in the same manner as in Example 6-(1) to give 1-(2-chloro-4-pyridyl)-2,3-bis (hydroxymethyl)-6-butoxy-7-methoxynaphthalene.

M.p. 93–97° C.

(2) 1-(2-Chloro-4-pyridyl)-2,3-bis(hydroxymethyl)-6-butoxy-7-methoxynaphthalene is treated in the same manner as in Example 104-(2) to give 1-(2-hydrazino-4-pyridyl)-2,3-bis(hydroxymethyl)-6-butoxy-7-methoxynaphthalene.

M.p. 93–97° C.

(3) 1-(2-Hydrazino-4-pyridyl)-2,3-bis(hydroxymethyl)-6-butoxy-7-methoxynaphthalene is treated in the same manner as in Example 104-(3) to give 1-[2-{4-(3-pyridyl)-1(2H)-phthalazinon-2-yl}-4-pyridyl]-2,3-bis(hydroxymethyl)-6-butoxy-7-methoxynaphthalene hydrochloride, which is listed in Table 12.

M.p. 198–201° C. (decomposed)

EXAMPLE 120

(1) 1-(2-Chloro-4-pyridyl)-2,3-bis(methoxycarbonyl)-6-octyloxy-7-methoxynaphthalene is treated in the same manner as in Example 6-(1) to give 1-(2-chloro-4-pyridyl)-2,3-bis(hydroxymethyl)-6-octyloxy-7-methoxynaphthalene.

M.p. 98–102° C.

(2) 1-(2-Chloro-4-pyridyl)-2,3-bis(hydroxymethyl)-6-octyloxy-7-methoxynaphthalene is treated in the same manner as in Example 104-(2) to give 1-(2-hydrazino-4-pyridyl)-2,3-bis(hydroxymethyl)-6-octyloxy-7-methoxynaphthalene.

M.p. 98–102° C.

(3) 1-(2-Hydrazino-4-pyridyl)-2,3-bis(hydroxymethyl)-6-octyloxy-7-methoxynaphthalene is treated in the same manner as in Example 104-(3) to give 1-[2-}4-(3-pyridyl)-1(2H)-phthalazinon-2-yl}-4-pyridyl]-2,3-bis(hydroxymethyl)-6-octyloxy-7-methoxynaphthalene hydrochloride, which is listed in Table 12.

M.p. 190–193° C. (decomposed)

EXAMPLE 121

1-(2-Chloro-4-pyridyl)-2,3-bis(hydroxymethyl)-6,7-dimethoxynaphthalene is treated in the same manner as in Example 104-(2) to give 1-(2-hydrazino-4-pyridyl)-2,3-bis (hydroxymethyl)-6,7-dimethoxynaphthalene, which is further treated together with the corresponding starting compound [VII] in the same manner as in Example 104-(3) to give crude 1-[2-{4-(3-pyridyl)-1(2H)-phthalazinon-2-yl}-4-pyridyl]-2,3-bis(hydroxymethyl)-6,7-dimethoxynaphthalene (75.5 g). This crude product is dissolved in chloroform-methanol (3:1, 700 ml), and the solution is treated with active carbon (3.7 g) and washed with a mixture of chloroform and methanol (3:1, 300 ml). To the mixture is added a 2M hydrochloric acid (69 ml), and the mixture is concentrated under reduced pressure to remove the solvent, and the resultant is subjected to azeotrophic distillation with ethanol (150 ml) twice, and concentrated under reduced pressure to remove the solvent. The precipitated crystals are collected by filtration, washed with ethanol (200 ml), and air-dried at 50° C. overnight to give 1-[2-{4-(3-pyridyl)-1(2H)-phthalazinon-2-yl}-4-pyridyl]-2,3-bis (hydroxymethyl)-6,7-dimethoxynaphthalene hydrochloride (84 g). To a solution of this product in chloroform-methanol (3:1, 1000 ml) is added an aqueous potassium carbonate solution (potassium carbonate (23 g) in water (300 ml)), and the organic layer is separated, dried, and the filtrate is concentrated under reduced pressure but so as not to precipitate the crystals. To the resultant is added ethanol (300 ml), and a part of the mixture is concentrated under reduced pressure to remove about 80% of chloroform and methanol. To the resultant is added ethanol (300 ml) again, and the mixture is concentrated to completely remove the solvent. The precipitates are collected by filtration, washed with ethanol (300 ml), and air-dried at 50° C. overnight to give 1-[2-{4-(3-pyridyl)-1(2H)-phthalazinon-2-yl}-4-pyridyl]-2,3-bis(hydroxymethyl)-6,7-dimethoxynaphthalene (66.6 g, yield; 85%), which is listed in Table 12.

M.p. 269–270° C.
Sulfate:
M.p. >260° C.

EXAMPLE 122

1-(2-Hydrazino-4-pyridyl)-2,3-bis(hydroxymethyl)-6,7-diethoxynaphthalene and the corresponding starting compound [VII] are treated in the same manner as in Example 104-(3) to give crude 1-[2-{4-(3-pyridyl)-1(2H)-phthalazinon-2-yl}-4-pyridyl]-2,3-bis(hydroxymethyl)-6,7-diethoxynaphthalene (6.5 g). This product is suspending in a mixture of ethanol (33 ml) and water (13 ml) at room temperature, and thereto is added dropwise 35% hydrochloric acid (2.2 ml), and the mixture is warmed to 50–55° C. The mixture is treated with active carbon (1.3 g), and the active carbon is removed by filtration and washed with a mixture of ethanol (13 ml) and water (7 ml). The filtrate is warmed to 45–50° C., and thereto is-added dropwise an aqueous sodium hydroxide solution (sodium hydroxide (1 g) in water (13 ml)), and the mixture is stirred at 55–60° C. for three hours, and an anhydride compound is added thereto. The mixture is stirred at room temperature overnight, and cooled with ice. The precipitates are collected by filtration, washed with 50% ethanol (13 ml), and air-dried at 50° C. overnight to give 1-[2-{4-(3-pyridyl)-1(2H)-phthalazinon-2-yl}-4-pyridyl]-2,3-bis(hydroxymethyl)-6,7-diethoxynaphthalene (5.6 g, yield; 86%), which is listed in Table 12.

M.p. 222° C.
Sulfate:
M.p. >220° C.
Methanesulfonate:
M.p. 160–163° C. (decomposed)

EXAMPLE 123

1-(2-Hydrazino-4-pyridyl)-2,3-bis(hydroxymethyl)-6,7-diethoxynaphthalene is treated in the same manner as in Example 104-(3) to give crude 1-[2-{4-(3-pyridyl)-1(2H)-phthalazinon-2-yl}4-pyridyl]-2,3-bis(hydroxymethyl)-6,7-diethoxynaphthalene (7.0 g). This product is suspended in a mixture of ethanol (35 ml) and water (14 ml) at room temperature. The suspension is dissolved by adding dropwise thereto 35% hydrochloric acid (2.3 ml), and the mixture is warmed to 50–55° C. The mixture is treated with active carbon (1.4 g), and the active carbon is removed by filtration and washed with a mixture of ethanol (14 ml) and water (7 ml). The filtrate is warmed to 35° C., and thereto is added dropwise an aqueous sodium hydroxide solution (sodium hydroxide (1.1 g) in water (14 ml)), and thereto is added a dihydrate compound. The mixture is stirred under ice-cooling for one hour, and the precipitates are collected by filtration, washed with 50% ethanol (14 ml), and air-dried at 50° C. overnight to give 1-[2-{4-(3-pyridyl)-1(2H)-phthalazinon-2-yl}-4-pyridyl]-2,3-bis(hydroxymethyl)-6,7-diethoxynaphthalene dihydrate (6.4 g, yield; 86%), which is listed in Table 12.

M.p. 141° C. (melting at 141° C., and being crystallized again as an anhydride form when heating more, and melting again at 222–223° C.)

EXAMPLE 124

(1) 1-(2-Chloro-4-pyridyl)-3-methoxycarbonyl-6,7-dimethoxynaphthalene is treated in the same manner as in Example 6-(1) to give 1-(2-chloro-4-pyridyl)-3-hydroxymethyl-6,7-dimethoxynaphthalene.

M.p. 115–118° C.

(2) 1-(2-Chloro-4-pyridyl)-3-hydroxymethyl-6,7-dimethoxynaphthalene is treated in the same manner as in Example 104-(2) to give 1-(2-hydrazino-4-pyridyl)-3-hydroxymethyl-6,7-dimethoxynaphthalene.

M.p. 139–144° C.

(3) 1-(2-Hydrazino-4-pyridyl)-3-hydroxymethyl-6,7-dimethoxynaphthalene is treated in the same manner as in Example 104-(3) to give 1-[2-{4-(3-pyridyl)-1(2H)-phthalazinon-2-yl}-1-pyridyl]-3-hydroxymethyl-6,7-dimethoxynaphthalene hydrochloride, which is listed in Table 13.

M.p. >250° C.

EXAMPLE 125

(1) To a suspension of 1-(2-chloro-4-pyridyl)-3-carboxy-6,7-diethoxynaphthalene in tetrahydrofuran (50 ml) is added dropwise a solution of 70% sodium aluminum bis(2-methoxyethoxy) hydride (70% toluene solution, 29.4 ml) in tetrahydrofuran (50 ml) at a temperature below 5° C. under nitrogen atmosphere, and the mixture is reacted at the same temperature for one hour. After the reaction is complete, to the mixture is added methanol (12 ml), and further thereto is added a 6.25 M aqueous sodium hydroxide solution (48 ml), and the mixture is stirred at 50° C. for one hour. The tetrahydrofuran layer is separated from the mixture, and the aqueous solution is extracted with methylene chloride, and the methylene chloride layer is separated, and combined with the tetrahydrofuran layer, then concentrated under reduced pressure. The resultant is extracted again with methylene chloride, washed, dried, and concentrated under reduced pressure. The residue is purified by silica gel column chromatography (solvent; chloroform:ethyl acetate= 4:1), and crystallized from ether to give 1-(2-chloro-4-pyridyl)-3-hydroxymethyl-6,7-diethoxynaphthalene (3.94 g).

M.p. 135–137° C.

(2) A suspension of 1-(2-chloro-4-pyridyl)-3-hydroxymethyl-6,7-diethoxynaphthalene (3.90 g) in hydrazine hydrate (17.8 ml) is refluxed for 9 hours. The mixture is stirred at room temperature for 10 minutes, and further stirred under ice-cooling for 10 minutes. To the mixture are added methylene chloride and water, and the methylene chloride layer is separated, washed, dried, and concentrated under reduced pressure to remove the solvent. The residue is dissolved in hot ethanol (20 ml), and allowed to cool overnight to give 1-(2-hydrazino-4-pyridyl)-3-hydroxymethyl-6,7-diethoxynaphthalene (3.19 g).

M.p. 147–149° C.

(3) 1-(2-Hydrazino-4-pyridyl)-3-hydroxymethyl-6,7-diethoxynaphthalene is treated in the same manner as in Example 104-(3) to give 1-[2-{4–3-pyridyl)-1(2H)-phthalazinon-2-yl )-4-pyridyl}-3-hydroxymethyl-6,7-diethoxynaphthalene hydrochloride (1.45 cg), which is listed in Table 14.

M.p. 197–201° C. (decomposed)

EXAMPLE 126

1-(2-Hydrazino-4-pyridyl)-3-hydroxymethyl-6,7-diethoxynaphthalene (177 mg), 1-carboxy-2-phenylcarbonylbenzene (191 mg) and ethylene glycol (1 ml) are treated in the same manner as in Example 104-(3) to give 1-{2-(4-phenyl-1(2H)-phthalazinon-2-yl)-4-pyridyl}-3-hydroxymethyl-6,7-diethoxynaphthalene (206 mg), which is listed in Table 14.

M.p. 203–204° C.

EXAMPLE 127

1-(2-Hydrazino-4-pyridyl)-3-hydroxymethyl-6,7-diethoxynaphthalene (177 mg), 1-carboxy-2-(4- chlorophenylcarbonyl)benzene (137 mg) and ethylene glycol (1 ml) are treated in the same manner as in Example 104-(3) to give 1-[2-{4-(4-chlorophenyl)-1(2H)-phthalazinon-2-yl}-4-pyridyl]-3-hydroxymethyl-6,7-diethoxynaphthalene (247 mg), which is listed in Table 14.

M.p. 223–225° C.

EXAMPLE 128

1-(2-Hydrazino-4-pyridyl)-3-hydroxymethyl-6,7-diethoxynaphthalene (177 mg), 1-carboxy-2-methylcarbonylbenzene (86 mg) and ethylene glycol (1 ml) are treated in the same manner as in Example 104-(3) to give 1-{2-(4-methyl-1(2H)-phthalazinon-2-yl)-4-pyridyl}-3-hydroxymethyl-6,7-diethoxynaphthalene (211 mg), which is listed in Table 14.

M.p. 220–221° C.

Reference Example 1

(1) 3,4-Dimethoxybenzaldehyde (398.8 g) is dissolved in acetic acid (1.8 liter), and thereto is added dropwise bromine (136 ml) at room temperature over a period of four hours. The mixture is stirred overnight, and thereto is added dropwise slowly again bromine (60 ml), and the mixture is stirred overnight. The reaction solution is added to water (7 liters), and the precipitated crystals are collected by filtration, washed with water, and dissolved in chloroform (2 liters). The chloroform solution is washed, dried, concentrated, and the residue is crystallized from dilsopropyl ether to give 6-bromo-3,4-dimethoxybenzaldehyde (470 g) as a colorless crystal.

M.p. 144–146° C.

(2) 6-Bromo-3,4-dimethoxybenzaldehyde (470 g) is suspended in methanol (600 ml), and thereto are added trimethyl orthoformate (1025 ml) and IRA-120 ($H^+$-type, 10 g), and the mixture is refluxed for one hour. The mixture is cooled to room temperature, and the insoluble materials are removed by filtration, and the filtrate is concentrated under reduced pressure. The resulting residue is dissolved in ether, washed, dried, evaporated to remove the ether, and distilled under reduced pressure to give 6-bromo-3,4-dimethoxybenzaldehyde dimethyl acetal (522 g) as a main distillate (133–138° C./1 Torr).

Reference Example 2

3,4-Diethoxybenzaldehyde is treated in the same manner as in Reference Example 1 to give 6-bromo-3,4-diethoxybenzaldehyde dimethyl acetal.

B.p. 145–150° C./1 Torr

Reference Example 3

3-Methoxy-4-ethoxybenzaldehyde is treated in the same manner as in Reference Example 1 to give 6-bromo-3-methoxy-4-ethoxybenzaldehyde dimethyl acetal.

B.p. 160–162° C./2 Torr

Reference Example 4

Benzaldehyde is treated in the same manner as in Reference Example 1 to give 2-bromobenzaldehyde dimethyl acetal.

B.p. 90–100° C./1 Torr

Reference Example 5

3-Ethoxy-4-methoxybenzaldehyde is treated in the same manner as in Reference Example 1 to give 6-bromo-3-ethoxy-4-methoxybenzaldehyde dimethyl acetal.

B.p. 170–175° C./3 Torr

Reference Example 6

A solution of 6-bromo-3,4-dimethoxybenzaldehyde dimethyl acetal (20 ml) in tetrahydrofuran (100 ml) is cooled to −60° C., and thereto is added dropwise a 1.6 M solution of n-butyl lithium in hexane (45.1 ml) over a period of 20 minutes under nitrogen atmosphere. The mixture is reacted at the same temperature for 30 minutes, and thereto is added dropwise a solution of 4-formylpyridine (7.36 g) in tetrahydrofuran (50 ml) over a period of 20 minutes. The reaction mixture is reacted for one hour, and thereto are added water and ethyl acetate (200 ml). The ethyl acetate layer is separated, washed, dried, and concentrated under reduced pressure to remove the ethyl acetate to give 3,4-dimethoxy-6-(4-pyridyl)hydroxymethylbenzaldehyde dimethyl acetal (15.4 g).

M.p. 130–133° C.

Reference Example 7

6-Bromo-3,4-diethoxybenzaldehyde dimethyl acetal is treated in the same manner as in Reference Example 6 to give 3,4-diethoxy-6-(4-pyridyl)hydroxymethylbenzaldehyde dimethyl acetal.

M.p. 108–109° C.

Reference Example 8

6-Bromo-3-methoxy-4-ethoxybenzaldehyde dimethyl acetal is treated in the same manner as in Reference Example 6 to give 3-methoxy-4-ethoxy-6-(4-pyridyl)hydroxymethylbenzaldehyde dimethyl acetal.

M.p. 125–127° C.

Reference Example 9

2-Bromobenzaldehyde dimethyl acetal is treated in the same manner as in Reference Example 6 to give 6-(4-pyridyl)hydroxymethylbenzaldehyde dimethyl acetal.

M.p. 115–116° C.

Reference Example 10

6-Bromo-3-ethoxy-4-methoxybenzaldehyde dimethyl acetal is treated in the same manner as in Reference Example 6 to give 3-ethoxy-4-methoxy-6-(4-pyridyl)hydroxymethylbenzaldehyde dimethyl acetal.

M.p. 114–115° C.

Reference Example 11

6-Bromo-3,4-dimethoxybenzaldehyde dimethyl acetal and 2-bromo-4-formylpyridine are treated in the same manner as in Reference Example 6 to give 3,4-dimethoxy-6-(2-bromo-4-pyridyl)hydroxymethylbenzaldehyde dimethyl acetal as an oily product.

Reference Example 12

6-Bromo-3,4-dimethoxybenzaldehyde dimethyl acetal and 2-formylpyridine are treated in the same manner as in Reference Example 6 to give 3,4-dimethoxy-6-(2-pyridyl)hydroxymethylbenzaldehyde dimethyl acetal as an oily product.

Reference Example 13

6-Bromo-3,4-dimethoxybenzaldehyde dimethyl acetal and 3-formyl-pyridine are treated in the same manner as in Reference Example 6 to give 3,4-dimethoxy-6-(3-pyridyl)hydroxymethylbenzaldehyde dimethyl acetal as an oily product.

Reference Example 14

To a solution of 3,4-dimethoxy-6-(4-pyridyl) hydroxymethylbenzaldehyde dimethyl acetal (18.4 g) in a mixture of acetic acid (50 ml) and toluene (50 ml) is added maleic acid dimethyl ester (8.64 ml), and the mixture is refluxed for one hour. To the mixture is added methanesulfonic acid (9.33 ml), and the mixture is refluxed for 8 hours while the generated water is removed by using a Dean-stark apparatus. The mixture is cooled to room temperature and concentrated. The residue is dissolved in chloroform, and the pH value thereof is adjusted to pH 8 with an aqueous potassium carbonate solution. The mixture is extracted with chloroform, and the extract is washed, dried, concentrated, and the residue is crystallized from ether to give 1-(4-pyridyl)-2,3-bis(methoxycarbonyl)-6,7-dimethoxynaphthalene (13.5 g).

M.p. 204–206° C.

Reference Example 15

3,4-Diethoxy-6-(4-pyridyl)hydoxymethylbenzaldehyde dimethyl acetal is treated in the same manner as in Reference Example 14 to give 1-(4-pyridyl)-2,3-bis (methoxycarbonyl)-6,7-diethoxynaphthalene.

M.p. 149–150° C.

Reference Example 16

3-Methoxy-4-ethoxy-6-(4-pyridyl) hydoxymethylbenzaldehyde dimethyl acetal is treated in the same manner as in Reference Example 14 to give 1-(4-pyridyl)-2,3-bis(methoxycarbonyl)-6-methoxy-7-ethoxynaphthalene.

M.p. 195–197° C.

Reference Example 17

6-(4-Pyridyl)hydoxymethylbenzaldehyde dimethyl acetal is treated in the same manner as in Reference Example 14 to give 1-(4-pyridyl)-2,3-bis(methoxycarbonyl)naphthalene.

M.p. 197–198° C.

Reference Example 18

3-Ethoxy-4-methoxy-6-(4-pyridyl) hydoxymethylbenzaldehyde dimethyl acetal is treated in the same manner as in Reference Example 14 to give 1-(4-pyridyl)-2,3-bis(methoxycarbonyl)-6-ethoxy-7-methoxynaphthalene.

M.p. 188–189° C.

Reference Example 19

3,4-Dimethoxy-6-(2-pyridyl)hydoxymethylbenzaldehyde dimethyl acetal is treated in the same manner as in Reference Example 14 to give 1-(2-pyridyl)-2,3-bis (methoxycarbonyl)-6,7-dimethoxynaphthalene.

M.p. 163–165° C.

Reference Example 20

3,4-Dimethoxy-6-(3-pyridyl)hydoxymethylbenzaldehyde dimethyl acetal is treated in the same manner as in Reference Example 14 to give 1-(3-pyridyl)-2,3-bis (methoxycarbonyl)-6,7-dimethoxynaphthalene.

M.p. 95–96° C.

Reference Example 21

To a solution of 1-(4-pyridyl)-2,3-bis(methoxycarbonyl)-6,7-dimethoxynaphthalene (5 g) in methylene chloride (300 ml) is added m-chloroperbenzoic acid (8.1 g) under ice-cooling, and the mixture is warmed to room temperature and stirred overnight. The reaction mixture is washed, dried, and concentrated to give 1-(4-pyridyl)-2,3-bis (methoxycarbonyl)-6,7-dimethoxynaphthalene N-oxide (15.0 g) as a crystal.

M.p. 237–239° C.

Reference Example 22

1-(4-Pyridyl)-2,3-bis(methoxycarbonyl)-6,7-diethoxynaphthalene is treated in the same manner as in Reference Example 21 to give 1-(4-pyridyl)-2,3-bis (methoxycarbonyl)-6,7-diethoxynaphthalene N-oxide.

M.p. 177–178° C.

Reference Example 23

1-(4-Pyridyl)-2,3-bis(methoxycarbonyl)-6-methoxy-7-ethoxynaphthalene is treated in the same manner as in Reference Example 21 to give 1-(4-pyridyl)-2,3-bis (methoxycarbonyl)-6-methoxy-7-ethoxynaphthalene N-oxide.

M.p. >220° C.

Reference Example 24

1-(4-Pyridyl)-2,3-bis(methoxycarbonyl)naphthalene is treated in the same manner as in Reference Example 21 to give 1-(4-pyridyl)-2,3-bis(methoxycarbonyl)naphthalene N-oxide.

M.p. 215–218° C.

Reference Example 25

1-(4-Pyridyl)-2,3-bis(methoxycarbonyl)-6-ethoxy-7-methoxynaphthalene is treated in the same manner as in Reference Example 21 to give 1-(4-pyridyl)-2,3-bis (methoxycarbonyl)-6-ethoxy-7-methoxynaphthalene N-oxide.

M.p. 230–231° C.

Reference Example 26

1-(2-Pyridyl)-2,3-bis(methoxycarbonyl)-6,7-dimethoxynaphthalene is treated in the same manner as in Reference Example 21 to give 1-(2-pyridyl)-2,3-bis (methoxycarbonyl)-6,7-dimethoxynaphthalene N-oxide.

M.p. 173–175° C.

Reference Example 27

1-(3-Pyridyl)-2,3-bis(methoxycarbonyl)-6,7-dimethoxynaphthalene is treated in the same manner as in Reference Example 21 to give 1-(3-pyridyl)-2,3-bis (methoxycarbonyl)-6,7-dimethoxynaphthalene N-oxide.

M.p. 185–186° C. (decomposed)

Reference Example 28

To tetrahydrofuran (25 ml) is added a 3.4 M solution of sodium aluminum bis(methoxyethxoy) hydride in toluene (18.0 ml), and the mixture is cooled to −10C. To the mixture is added dropwise a suspension of 1-(4-pyridyl)-2,3-bis (methoxycarbonyl)-6,7-diethoxynaphthalene (10.0 g) in tetrahydrofuran (25 ml) over a period of 15 minutes. The reaction solution is warmed, and stirred under ice-cooling for 1.5 hour, and thereto is added a 15% aqueous sodium hydroxide solution (3.7 ml). To the reaction mixture are added water and methylene chloride, and the insoluble materials are removed by filtration. The filtrate is extracted with methylene chloride, and the extract is washed, dried, and concentrated to give 1-(4-pyridyl)-2,3-bis (hydroxymethyl)-6,7-diethoxynaphthalene (7.89 g).

M.p. 159–161° C.

Reference Example 29

1-(4-Pyridyl)-2,3-bis(methoxycarbonyl)-6,7-dimethoxynaphthalene is treated in the same manner as in Reference Example 28 to give 1-(4-pyridyl)-2,3-bis (hydroxymethyl)-6,7-dimethoxynaphthalene.

M.p. 135–138° C.

Reference Example 30

1-(4-Pyridyl)-2,3-bis(hydroxymethyl)-6,7-diethoxynaphthalene (20.0 g is dissolved in methylene chloride (200 ml), and thereto are added dropwise acetic anhydride (46.6 g) and triethylamine (57.4 g,), and the mixture is stirred at room temperature overnight. The, mixture is diluted with methylene chloride, washed with water, dried, and concentrated. The residue is recrystallized from a mixture of ethyl acetate and hexane to give 1-(4-pyridyl)-2,3-bis(acetoxy-methyl)-6,7-diethoxynaphthalene (22.4g)

M.p. 115–116° C.

Reference Example 31

1-(4-Pyridyl)-2,3-bis(hydroxymethyl)-6,7-dimethoxynaphthalene is treated in the same manner as in Reference Example 30 to give 1-(4-pyridyl)-2,3-bis (acetoxymethyl)-6,7-dimethoxynaphthalene.

M.p. 165–167° C.

Reference Example 32

To a solution of 1-(4-pyridyl)-2,3-bis(acetoxymethyl)-6,7-diethoxynaphthalene (22.4 g)in methylene chloride- (100. ml) is added m-chloro-perbenzoic acid (19.0 g)at room temperature, and the mixture is stirred overnight. The, reaction solution is washed, dried, and concentrated. The residue is crystallized from ether to give 1-(4-pyridyl)-2,3-bis(acetoxymethyl)- 6,7-diethoxynaphthalene N-oxide (20.8 g).

M.p. 158–159° C.

Reference Example 33

1-(4-Pyridyl)-2,3-bis(acetoxymethyl)-6,7-dimethoxynaphthalene is treated in the same manner as in Reference Example 32 to give 1-(4-pyridyl)-2,3-bis (acetoxymethyl)-6,7-dimethoxynaphthalene N-oxide.

M.p. 182–185° C.

Reference Example 34

A mixture of 1-(4-pyridyl)-2,3-bis(methoxycarbonyl)-6,7-dimethoxynaphthalene N-oxide (30 g) and phosphorus oxychloride (150 ml) is refluxed for two hours. The mixture is concentrated under reduced pressure to remove the phosphorus oxychloride, and thereto are added methylene chloride and an aqueous potassium carbonate solution. The methylene chloride layer is separated, and concentrated under reduced pressure to remove the solvent. The resultant is crystallized from methanol to give 1-(2-chloro-4-pyridyl)-2,3-bis(methoxycarbonyl)-6,7-dimethoxynaphthalene (26 g).

M.p. 201–203° C.

Reference Example 35

1-(4-Pyridyl)-2,3-bis(methoxycarbonyl)-6-methoxy-7-ethoxy-naphthalene N-oxide is treated in the same manner as in Reference Example 34 to give 1-(2-chloro-4-pyridyl)-2,3-bis(methoxycarbonyl)-6-methoxy-7-ethoxy-naphthalene.

M.p. 196–198° C.

Reference Example 36

1-(4-Pyridyl)-2,3-bis(methoxycarbonyl)naphthalene N-oxide is treated in the same manner as in Reference Example 34 to give 1-(2-chloro-4-pyridyl)-2,3-bis (methoxycarbonyl)naphthalene.

M.p. 174–178° C.

Reference Example 37

1-(4-Pyridyl)-2,3-bis(methoxycarbonyl)-6-ethoxy-7-methoxynaphthalene N-oxide is treated in the same manner as in Reference Example 34 to give 1-(2-chloro-4-pyridyl)-2,3-bis(methoxycarbonyl)-6-ethoxy-7-methoxynaphthalene.

M.p. 205–208° C.

Reference Example 38

1-(4-Pyridyl)-2,3-bis(methoxycarbonyl)-6,7-diethoxynaphthalene N-oxide is treated in the same manner as in Reference Example 34 to give 1-(2-chloro-4-pyridyl)-2,3-bis(methoxycarbonyl)-6,7-diethoxynaphthalene.

M.p. 154–156° C.

Reference Example 39

1-(2-Pyridyl)-2,3-bis(methoxycarbonyl)-6,7-diethoxynaphthalene N-oxide is treated in the same manner as in Reference Example 34 to give a mixture of 1-(2-chloro-6-pyridyl)-2,3-bis(methoxycarbonyl)-6,7-dimethoxynaphthalene and 1-(4-chloro-2-pyridyl)-2,3-bis (methoxycarbonyl)-6,7-dimethoxynaphthalene.

MS: 415 (M$^+$)

Reference Example 40

1-(3-Pyridyl)-2,3-bis(methoxycarbonyl)-6,7-dimethoxynaphthalene N-oxide is treated in the same manner as in Reference Example 34 to give a mixture of 1-(2-chloro-5-pyridyl)-2,3-bis(methoxycarbonyl)-6,7-dimethoxynaphthalene and 1-(2-chloro-3-pyridyl)-2,3-bis (methoxycarbonyl)-6,7-dimethoxynaphthalene.

MS: 415 (M$^+$)

Reference Example 41

A mixture of 1-(2-chloro-4-pyridyl)-2,3-bis (methoxycarbonyl)-6,7-dimethoxynaphthalene (22.7 g), phosphorus tribromide (52 ml) and 1,1,2,2-tetrachloroethane (100 ml) is stirred at 100° C. for 10 hours. After the reaction is complete, the mixture is concentrated under reduced pressure to remove the solvent, and thereto are added methylene chloride and an aqueous potassium carbonate solution. The methylene chloride layer is separated, and concentrated under reduced pressure to remove the solvent. The residue is crystallized from methanol to give 1-(2-bromo-4-pyridyl)-2,3-bis (methoxycarbonyl)-6,7-dimethoxynaphthalene (17.1 g).

M.p. 192–194° C.

Reference Example 42

1-(2-Chloro-4-pyridyl)-2,3-bis(methoxycarbonyl) naphthalene is treated in the same manner as in Reference Example 41 to give 1-(2-bromo-4-pyridyl)-2,3-bis (methoxycarbonyl)naphthalene.

M.p. 162–163° C.

Reference Example 43

1-(2-Chloro-4-pyridyl)-2,3-bis(methoxycarbonyl)-6-ethoxy-7-methoxynaphthalene is treated in the same manner as in Reference Example 41 to give 1-(2-bromo-4-pyridyl)-2,3-bis(methoxycarbonyl)-6-ethoxy-7-methoxynaphthalene.

M.p. 203–204° C.

Reference Example 44

The mixture obtained in Reference Example 39 is treated in the same manner as in Reference Example 41, and purified by silica gel column chromatography to give 1-(2-bromo-6-pyridyl)-2,3-bis(methoxycarbonyl)-6,7-dimethoxynaphthalene.

M.p. 199–200° C.

Reference Example 45

The mixture obtained in Reference Example 40 is treated in the same manner as in Reference Example 41, and purified by silica gel column chromatography to give 1-(2-bromo-5-pyridyl)-2,3-bis(methoxycarbonyl)-6,7-dimethoxynaphthalene.

M.p. 182–184° C.

Reference Example 46

To a suspension of 1-(4-pyridyl)-2,3-bis (methoxycarbonyl)-6,7-dimethoxynaphthalene N-oxide (106.4 g) in 1,2-dichloroethane (500 ml) is added phosphorus oxychloride (100 g), and the mixture is refluxed for five hours. After the reaction is complete, the mixture is concentrated under reduced pressure, and thereto is added ethyl acetate. The ethyl acetate solution is poured into ice-water, and the precipitated crystals are collected by filtration to give 1-(2-bromo-4-pyridyl)-2,3-bis(methoxycarbonyl)-6,7-dimethoxynaphthalene (38.9 g).

M.p. 192–194° C.

Reference Example 47

3,4-Dimethoxy-6-(4-pyridyl) hydroxymethylbenzaldehyde dimethyl acetal and methyl crotonate are treated in the same manner as in Reference Example 14 to give 1-(4-pyridyl)-2-methoxycarbonyl-3-methyl-6,7-dimethoxynaphthalene.

M.p. 152–154° C.

Reference Example 48

3,4-Dimethoxy-6-(4-pyridyl) hydroxymethylbenzaldehyde dimethyl acetal and methyl acrylate are treated in the same manner as in Reference Example 14 to give 1-(4-pyridyl)-2-methoxycarbonyl-6,7-dimethoxynaphthalene.

M.p. 152–154° C.

Reference Example 49

1-(4-Pyridyl)-2-methoxycarbonyl-3-methyl-6,7-dimethoxynaphthalene is treated in the same manner as in Reference Example 21 to give 1-(4-pyridyl)-2-methoxycarbonyl-3-methyl-6,7-dimethoxynaphthalene N-oxide.

M.p. 230–232° C.

Reference Example 50

1-(4-Pyridyl)-2-methoxycarbonyl-6,7-dimethoxynaphthalene is treated in the same manner as in Reference Example 21 to give 1-(4-pyridyl)-2-methoxycarbonyl-6,7-dimethoxynaphthalene N-oxide.

M.p. 222–224° C.

Reference Example 51

1-(4-Pyridyl)-2-methoxycarbonyl-3-methyl-6,7-dimethoxynaphthalene N-oxide is treated in the same manner as in Reference Example 34 to give 1-(2-chloro-4-pyridyl)-2-methoxycarbonyl-3-methyl-6,7-dimethoxynaphthalene.

M.p. 133–136° C.

Reference Example 52

1-(4-Pyridyl)-2-methoxycarbonyl-6,7-dimethoxynaphthalene N-oxide is treated in the same manner as in Reference Example 34 to give 1-(2-chloro-4-pyridyl)-2-methoxycarbonyl-6,7-dimethoxynaphthalene.

M.p. 142–145° C.

Reference Example 53

1-(2-Chloro-4-pyridyl)-2-methoxycarbonyl-3-methyl-6,7-dimethoxynaphthalene is treated in the same manner as in Reference Example 41 to give 1-(2-bromo-4-pyridyl)-2-methoxycarbonyl-3-methyl-6,7-dimethoxynaphthalene.

M.p. 148–150° C.

Reference Example 54

1-(2-Chloro-4-pyridyl)-2-methoxycarbonyl-6,7-dimethoxynaphthalene is treated in the same manner as in Reference Example 41 to give 1-(2-bromo-4-pyridyl)-2-methoxycarbonyl-6,7-dimethoxynaphthalene.

M.p. 146–148° C.

Reference Example 55

To a solution of isovanillin (200 g) in dimethylformamide (500 ml) is added potassium carbonate (236 g) under ice-cooling, and thereto is added dropwise benzyl bromide (203 ml), and the mixture is stirred overnight. The insoluble materials in the resulting residue are removed by filtration, and washed with acetone, and the filtrate is concentrated under reduced pressure to remove the solvent. The residue is washed again with ether and water, and concentrated under reduced pressure to remove the solvent to give 3-benzyloxy-4-methoxybenzaldehyde as an oily product.

Reference Example 56

(1) 3-Benzyloxy-4-methoxybenzaldehyde is treated in the presence of sodium acetate in the same manner as in Reference Example 1-(1) to give 6-bromo-3-benzyloxy4-methoxybenzaldehyde as a colorless crystal.

M.p. 140–141° C.

(2) 6-Bromo-3-benzyloxy-4-methoxybenzaldehyde is treated in the same manner as in Reference Example 1-(2) to give 6-bromo-3-benzyloxy-4-methoxybenzaldehyde dimethyl acetal as an oily product.

Reference Example 57

6-Bromo-3-benzyloxy-4-methoxybenzaldehyde dimethyl acetal is treated in the same manner as in Reference Example 6 to give 3-benzyloxy-4-methoxy-6-(4-pyridyl) hydroxymethylbenzaldehyde dimethyl acetal as an oily product.

Reference Example 58

3-Benzyloxy-4-methoxy-6-(4-pyridyl) hydroxymethylbenzaldehyde dimethyl acetal is treated at room temperature for three days in the same manner as in Reference Example 14 to give 1-(4-pyridyl)-2,3-bis (methoxycarbonyl)-6-benzyloxy-7-methoxynaphthalene.

M.p. 240–242° C. (decomposed)

Reference Example 59

1-(4-Pyridyl)-2,3-bis(methoxycarbonyl)-6-benzyloxy-7-methoxynaphthalene is treated in the same manner as in Reference Example 21 to give 1-(4-pyridyl)-2,3-bis (methoxycarbonyl)-6-benzyloxy-7-methoxynaphthalene N-oxide.

M.p. 254–257° C. (decomposed)

Reference Example 60

1-(4-Pyridyl)-2,3-bis(methoxycarbonyl)-6-benzyloxy-7-methoxynaphthalene N-oxide is treated in the same manner as in Reference Example 34 to give 1-(2-chloro-4-pyridyl)-2,3-bis(methoxycarbonyl)-6-benzyloxy-7-methoxynaphthalene.

M.p. 260–261° C. (decomposed)

Reference Example 61

1-(4-Pyridyl)-2,3-bis(methoxycarbonyl)-6-benzyloxy-7-methoxynaphthalene is treated in the same manner as in Reference Example 117-(1) to give 1-(4-pyridyl)-2,3-bis (methoxycarbonyl)-6-hydroxy-7-methoxynaphthalene.

M.p. 225–230° C. (decomposed)

Reference Example 62

1-(4-Pyridyl)-2,3-bis(methoxycarbonyl)-6-hydroxy-7-methoxynaphthalene and isopropyl iodide are treated in the same manner as in Reference Example 117-(2) to give 1-(4-pyridyl)-2,3-bis(methoxycarbonyl)-6-isopropyloxy-7-methoxynaphthalene.

M.p. 210–212° C.

Reference Example 63

1-(4-Pyridyl)-2,3-bis(methoxycarbonyl)-6-hydroxy-7-methoxynaphthalene and butyl iodide are treated in the same manner as in Reference Example 117-(2) to give 1-(4-pyridyl)-2,3-bis(methoxycarbonyl)-6-butoxy-7-methoxynaphthalene.

M.p. 149–151° C.

Reference Example 64

1-(4-Pyridyl)-2,3-bis(methoxycarbonyl)-6-hydroxy-7-methoxynaphthalene and octyl iodide are treated in the same manner as in Reference Example 117-(2) to give 1-(4-pyridyl)-2,3-bis(methoxycarbonyl)-6-octyloxy-7-methoxynaphthalene.

M.p. 124–126° C.

Reference Example 65

1-(4-Pyridyl)-2,3-bis(methoxycarbonyl)-6-isopropyloxy-7-methoxynaphthalene is treated in the same manner as in Reference Example 21 to give 1-(4-pyridyl)-2,3-bis (methoxycarbonyl)-6-isopropyloxy-7-methoxynaphthalene N-oxide.

M.p. 195–200° C. (decomposed)

Reference Example 66

1-(4-Pyridyl)-2,3-bis(methoxycarbonyl)-6-butoxy-7-methoxynaphthalene is treated in the same manner as in Reference Example 21 to give 1-(4-pyridyl)-2,3-bis (methoxycarbonyl)-6-butoxy-7-methoxynaphthalene N-oxide.

M.p. 170–173° C.

Reference Example 67

1-(4-Pyridyl)-2,3-bis(methoxycarbonyl)-6-octyloxy-7-methoxynaphthalene is treated in the same manner as in Reference Example 21 to give 1-(4-pyridyl)-2,3-bis (methoxycarbonyl)-6-octyloxy-7-methoxynaphthalene N-oxide.

M.p. 143–146° C.

Reference Example 68

1-(4-Pyridyl)-2,3-bis(methoxycarbonyl)-6-isopropyloxy-7-methoxynaphthalene N-oxide is treated in the same manner as in Reference Example 34 to give 1-(2-chloro-4-pyridyl)-2,3-bis(methoxycarbonyl)-6-isopropyloxy-7-methoxynaphthalene.

M.p. 195–200° C. (decomposed)

Reference Example 69

1-(4-Pyridyl)-2,3-bis(methoxycarbonyl)-6-butoxy-7-methoxynaphthalene N-oxide is treated in the same manner as in Reference Example 34 to give 1-(2-chloro-4-pyridyl)-2,3-bis(methoxycarbonyl)-6-butoxy-7-methoxynaphthalene.

M.p. 143–147° C.

Reference Example 70

1-(4-Pyridyl)-2,3-bis(methoxycarbonyl)-6-octyloxy-7-methoxynaphthalene N-oxide is treated in the same manner as in Reference Example 34 to give 1-(2-chloro-4-pyridyl)-2,3-bis(methoxycarbonyl)-6-octyloxy-7-methoxynaphthalene.

M.p. 93–97° C.

Reference Example 71

4-Carboxy-2-chloropyridine (78.7 g) is added slowly to a suspension of sodium borohydride (28.4 g) in tetrahydrofuran (750 ml) under nitrogen atmosphere, and thereto is added dropwise boron trifluoride-ether complex (123 ml). The mixture is reacted at room temperature for six hours. To the mixture is added a 6 M hydrochloric acid (960 ml), and the mixture is concentrated under reduced pressure to remove the solvent. The resultant is basified with sodium hydroxide, and extracted with chloroform, The chloroform layer is washed with a saturated aqueous sodium hydrogen carbonate solution, dried and concentrated under reduced pressure to remove the solvent to give 2-chloro-4-hydroxymethylpyridine (62.2 g).

M.p. 63–65° C.

Reference Example 72

(1) To a solution of oxalyl chloride (42.2 ml) in methylene chloride (1100 ml) is added dropwise a solution of dimethyl sulfoxide (68.7 ml) in methylene chloride (220 ml) at −60° C. to −50° C., and thereto is further added dropwise a solution of 2-chloro-4-hydroxymethylpyridine (63.2 g) in methylene chloride (440 ml) at the same temperature. The mixture is stirred for 15 minutes, and thereto is added dropwise triethylamine (306.6 ml) at the same temperature. The mixture is stirred for five minutes, and warmed to room temperature. After the reaction is complete, to the reaction mixture is added water (2.2 liters). The methylene chloride layer is separated, and the aqueous layer is extracted again with methylene chloride (2.2 liters). The methylene chloride layers are combined, and washed with a saturated aqueous sodium hydrogen carbonate solution, dried, and concentrated under reduced pressure to remove the solvent to give 2-chloropyridine-4-carbaldehyde.

(2) A solution of 2-chloropyridine-4-carbaldehyde in dimethylformamide (150 ml) is added dropwise into a suspension of sodium cyanide (5.2 g) in dimethylformamide (200 ml) over a period of five minutes. The mixture is stirred for five minutes, and thereto is added dropwise a solution of acrylic acid tert-butyl ester (61.4 ml) in dimethylformamide (350 ml) over a period of ten minutes, and the mixture is stirred overnight. To the reaction mixture are added ethyl acetate and water, and the ethyl acetate layer is washed with a saturated aqueous sodium hydrogen carbonate solution, dried, and concentrated under reduced pressure to remove the solvent. The residue is purified by silica gel column chromatography (solvent; hexane:ethyl acetate=4:1) to give 4-(2-chloropyridin- 4-yl)-4-oxo-butylic acid tert-butyl ester (82.8 g) as an oily product.

Reference Example 73

To 4-(2-chloropyridin-4-yl)-4-oxo-butylic acid tert-butyl ester (82.8 g) is added trifluoroacetic acid (118 ml) under ice-cooling, and the mixture is stirred for 15 minutes, and reacted at room temperature for one hour. To the mixture is further added trifluoroacetic acid (24 ml), and the mixture is reacted at room temperature for two hours. The mixture is concentrated under reduced pressure to remove the trifluoroacetic acid, subjected to azeotrophic distillation with toluene, and crystallized from ether to give 4-(2-chloropyridin-4-yl)-4-oxo-butylic acid (53.8 g).

M.p. 118–120° C.

Reference Example 74

A mixture of 3,4-dimethoxybenzaldehyde (1.66 g), 4-(2-chloropyridin-4-yl)-4-oxo-butylic acid (2.14 g), sodium acetate (0.82 g) and acetic anhydride (5.66 ml) is stirred at 80° C. for two hours. To the mixture are added dropwise acetic acid and conc. hydrochloric acid (50 ml), and the mixture is refluxed for two hours. The reaction solution is washed with ether, and the pH value of the mixture is adjusted to pH 4 with sodium hydroxide. The mixture is dried and concentrated under reduced pressure to remove the solvent. The residue is extracted with a mixture of chloroform and methanol (9:1) to give 1-(2-chloro-4-pyridyl)-3-carboxy-6,7-dimethoxynaphthalene-(yield; 67%), M.p. >250° C.

Reference Example 75

To a solution of 1-(2-chloro-4-pyridyl)-3-carboxy-6,7-dimethoxynaphthalene (2.3 g) in tetrahydrofuran (60 ml) is added dropwise a solution of sodium aluminum bis(2-methoxyethoxy) hydride (70% toluene solution, 2.36 ml) in tetrahydrofuran at −10° C., and the mixture is stirred at room temperature for one hour. To the mixture is added dropwise a solution of sodium aluminum bis(2-methoxyethoxy) hydride (70% toluene solution, 1.57 ml) in tetrahydrofuran (5 ml), and the mixture is heated with stirring at 40° C. for one hour. To the mixture is added methanol, and thereto is added an aqueous sodium hydroxide solution (sodium hydroxide (1.6 g) in water (20 ml)), and the mixture is stirred at 50° C. for 30 minutes. The reaction residue is extracted with ethyl acetate, and extracted with dichloromethane. The organic layer is washed with water, dried, and concentrated under reduced pressure to remove the solvent. The residue is purified by silica gel column chromatography (solvent; chloroform:acetone=19:1), and crystallized from ether to give 1-(2-chloro-4-pyridyl)-3-hydroxymethyl-6,7-dimethoxynaphthalene (531 mg, yield; 24%).

M.p. 115–118° C.

Reference Example 76

A mixture of 3,4-diethoxybenzaldehyde (54.2 g), 4-(2-chloropyridin-4-yl)-4-oxo-butylic acid (59.6 g), sodium acetate (22.9 g) and acetic anhydride (158 ml) is stirred at 80° C. for two hours under nitrogen atmosphere. The mixture is allowed to cool for 30 minutes, and thereto are added acetic acid (1.4 liter) and conc. hydrochloric acid (1.4 liter), and the mixture is refluxed for two hours. The mixture is cooled with ice, and thereto is added sodium hydroxide (672 g), and thereto are further added water-(1.4 liter), chloroform (2.5 liter), and methanol (0.3 liter). The chloroform layer is dried, concentrated under reduced pressure to remove the solvent, and the residue is crystallized from ether to give 1-(2-chloro-4-pyridyl)-3-carboxy-6,7-diethoxynaphthalene (70.4 g).

M.p. >250° C.

EFFECTS OF INVENTION

The desired compounds [I] of the present invention and a pharmaceutically acceptable salt thereof show an excellent bronchoconstriction inhibitory activity and are useful in the prophylaxis or treatment of asthma. That is, the desired compounds [I] of the present invention can effectively inhibit the bronchoconstriction induced by various spasmogens such as histamine, U-46619, leukotriene $D_4$, etc., or by antigens. For example, the desired compounds of the present invention such as 1-[2-(2-oxo-1,2-dihydroquinolin-1-yl)-4-pyridyl]-2,3-bis(hydroxymethyl)-6,7-dimethoxynaphthalene, 1-{2-[2-oxo-4-(2-piperidinoethyl)amino-1,2-dihydroquinolin-1-yl]-4-pyridyl}-2,3-bis(hydroxymethyl)-6,7-dimethoxynaphthalene, 1-{2-[2-oxo-4-(4-pyridyl)-1,2-dihydroquinolin-1-yl]-4-pyridyl}-2,3-bis(hydroxymethyl)-6,7-dimethoxynaphthalene, 1-[2-(2-oxo-3-morpholino-1,2-dihydroxyquinolin-1-yl)-4-pyridyl]-2,3-bis(hydroxymethyl)-6,7-dimethoxynaphthalene, 1-[2-(1-oxo-5-methoxymethoxy-1,2-dihydroisoquinolin-2-yl)-4-pyridyl]-2,3-bis(hydroxymethyl)-6,7-dimethoxynaphthalene, 1-{2-[1-oxo-5-(2-piperidinoethyloxy)-1,2-dihydroisoquinolin-2-yl]-4-pyridyl}-2,3-bis(hydroxymethyl)-6,7-dimethoxynaphthalene, 1-[2-(3-oxo-2,3-dihydroisoquinolin-2-yl)-4-pyridyl]-2,3-bis(hydroxymethyl)-6,7-dimethoxynaphthalene, 1-{2-[4-(3-pyridyl)-1(2H)-phthalazinon-2-yl]-4-pyridyl}-2,3-bis(hydroxymethyl)-6,7-dimethoxynaphthalene, 1-{2-[4-(3-pyridylmethyl)-1(2H)-phthalazinon-2-yl]-4-pyridyl}-2,3-bis(hydroxymethyl)-6,7-dimethoxynaphthalene, 1-{2-[6,7-dimethoxy-4-(3-pyridyl)- 1(2H)-phthalazinon-2-yl]-4-pyridyl}-2,3-bis(hydroxymethyl)-6,7-diethoxynaphthalene, 1-{2-[4-(3-pyridyl)- 1(2H)-phthalazinon-2-yl]-4-pyridyl}-

2,3-bis(hydroxymethyl])-6,7-diethoxynaphthalene, 1-{2-[4-(3-pyridyl)-1(2H)-phthalazinon-2-yl]-4-pyridyl}-2,3-bis(hydroxymethyl)-6-methoxy-7-ethoxynaphthalene, or a pharmaceutically acceptable salt thereof show antigen-induced broncho-constriction inhibitory activity more than 30 times as strong as those of theophylline.

Besides, the desired compounds [I] of the present invention and a pharmaceutically acceptable salt thereof hardly show any side effects on heart, etc., but selectively show bronchoconstriction inhibitory activity and low toxicity, and hence, they advantageously show high safety as a medicament. Although theophylline shows serious side effects on heart such hypotension, cardioplamus, etc., the desired compounds [I] of the present invention and a pharmaceutically acceptable salt thereof substantially do not show such side effects and only show an excellent antiasthmatic activity.

What is claimed:

1. A naphthalene derivative of the formula (I):

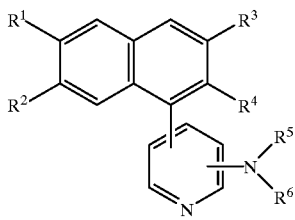

(I)

wherein $R^1$ and $R^2$ are the same or different and are each a hydrogen atom or a protected or unprotected hydroxy group; either one of $R^3$ and $R^4$ is a protected or unprotected hydroxy-substituted methyl group, and another is a hydrogen atom, a lower alkyl group, or a protected or unprotected hydroxy-substituted methyl group; $R^5$ and $R^6$ are both bond at their termini and combine with the adjacent nitrogen atom to form a substituted or unsubstituted isoquinolyl group that may be partially or wholly hydrogenated or, a five membered heterocyclicring, or a pharmaceutically acceptable salt thereof, with the proviso that $R^5$ and $R^6$ do not combine with the adjacent nitrogen atom to form phtharazinyl or quinolyl.

2. A compound according to claim 1, wherein $R^1$ and $R^2$ are the same or different and are each a hydrogen atom or a lower alkoxy group.

3. A compound according to claim 1 wherein the isoquinolyl group or five membered heterocyclic ring formed by combining $R^5$ and $R^1$ together with the adjacent nitrogen atom is substituted by one or more of the substituents selected from the group consisting of (1) a lower alkenyl group, (2) a lower alkynyl group, (3) a lower alkylthio group, (4) a cycloalkyl group, (5) a trifluoromethyl group, (6) a cyano group, (7) a tetrazolyl group, (8) a formyl group, (9) an amino group, (10) a mono- or di-lower alkylamino group in which the alkyl moiety is optionally substituted by a morpholino group, a monocycloalkyl-substituted amino group, a pyridyl group, an imidazolyl group, a piperidyl group, or a pyrrolidinyl group, (11) a pyridyl group, (12) a morpholino group, (13) a lower alkyl-substituted triazolyl group, (14) a bis(hydroxy-lower alkyl)aminocarbonyl group, (15) bis(tri-lower alkylsilyloxy-lower alkyl) aminocarbonyl group, (16) a morpholinocarbonyl group, (17) a lower alkyl-substituted piperazinylcarbonyl group, (18) a hydroxy-lower alkyl-substituted piperazinylcarbonyl group, (19) a tri-lower alkylsilyloxy-lower alkyl-substituted piperanzinylcarbonyl group, (20) a lower alkoxycarbonyl group, (21) a carboxyl group, (22) a lower alkyl group being optionally substituted by a morpholino group or a pyridyl group, (23) a lower alkoxyl group being optionally substituted by a piperidyl group, a pyridyl group, a hydroxy group or a lower alkoxy group, (24) an oxo group, (25) a hydroxy group, (26) a pyrimidinyl group, (27) a phenyl group being optionally substituted by a di-lower alkylamino group or a halogen atom, (28) a halogen atom, (29) a nitro group, (30) an imidazolyl group, and (31) a lower alkylenedioxy group.

4. A compound according to claim 5, wherein the isoquinolyl group or five membered heterocyclic ring, formed by combining $R^5$ and $R^6$ together with the adjacent nitrogen atom is an isoquinolyl group or a five membered heterocyclic ring having at least one oxo substituent.

5. A compound according to claim 4, wherein the isoquinolyl group or the five membered heterocyclic ring having at least one oxo substituent has a partial structure of the formula:

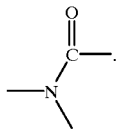

6. A compound according to claim 1, wherein $R^1$ and $R^2$ are the same or different and are each a protected hydroxy group, and $R^3$ and $R^4$ are each a hydroxy-substituted methyl group.

7. A compound according to claim 6, wherein the protected hydroxy group is a hydroxy group protected by an alkyl group.

8. A compound of the formula (VI):

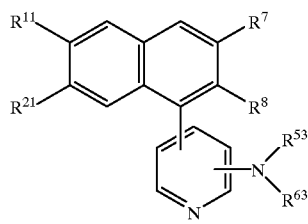

(VI)

wherein $R^{11}$ and $R^{21}$ are the same or different and are each a hydrogen atom or a protected or unprotected hydroxy group, either one of $R^7$ and $R^8$ is a free or esterified carboxyl group, and another one is a hydrogen atom, a lower alkyl group, or a free or esterified carboxyl group, and $R^{53}$ and $R^{63}$ are both combine together with the adjacent nitrogen atom to form a an isoquinolyl group, or a five membered heterocyclic ring being optionally substituted and being stable to a reduction reaction wherein said isoquinolyl group may be partially or wholly hydrogenated, with the proviso that $R^{53}$ and $R^{63}$ do not combine with the adjacent nitrogen atom to form phtharazinyl or quinolyl.

9. A compound according to claim 3, wherein the group formed by combining $R^5$ and $R^6$ together with the adjacent nitrogen atom is an isoquinolyl group selected from the group consisting of (1) an oxo- (or hydroxy-)substituted dihydro- (or tetrahydro-)- isoquinolyl group which may optionally be substituted by a member selected from a morpholino-substituted lower alkyl group; a lower alkoxy group having optionally a piperidyl, pyridyl or lower alkoxy substituent; and a hydroxy group, and (2) a dihydro- (or tetrahydro-)isoquinolyl group.

10. A compound according to claim 9, wherein the isoquinolyl group formed by combining $R^5$ and $R^6$ with the adjacent nitrogen atom is an oxo-substituted dihydroisoquinolyl group which may optionally be substituted by a member selected from a morpholino-substituted lower alkyl group; a lower alkoxy group having a piperidyl, pyridyl or lower alkoxy substituent; and a hydroxy group.

11. A compound according to claim 1, wherein the isoquinolyl group formed by combining $R^5$ and $R^6$ together with the adjacent nitrogen atom is selected from the group consisting of:
  (1) an oxo-substituted dihydro- (or tetrahydro-) isoquinolyl group, and
  (2) a dihydro- (or tetrahydro-) isoquinolyl group.

12. A compound according to claim 1, wherein the isoquinolyl group formed by combining $R^5$ and $R^6$ together with the adjacent nitrogen atom is selected from the group consisting of:
  (1) an oxo-substituted dihydro- isoquinolyl group, and
  (2) a tetrahydroisoquinolyl group.

13. A compound according to claim 1, wherein the compound is 1-{2-4-pyridyl}-2,3-bis(hydroxymethyl)-6,7-dimethoxynaphthalene, or a pharmaceutically acceptable salt thereof.

14. A process for the preparation of a naphthalene derivative of the formula (I''):

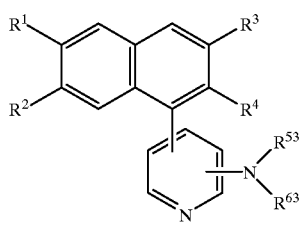

(I'')

wherein $R^1$ and $R^2$ are the same or different and are each a hydrogen atom or a protected or unprotected hydroxy group; either one of $R^3$ and $R^4$ is a protected or unprotected hydroxy-substituted methyl group, and another is a hydrogen atom, a lower alkyl group, or a protected or unprotected hydroxy-substituted methyl group; and $R^{53}$ and $R^{63}$ are the same or different and are each a hydrogen atom, a substituted or unsubstituted alkyl group, a substituted or unsubstituted phenyl group, or a protected or unprotected amino group, or both combine together with the adjacent nitrogen atom to form a quinolyl group, an isoquinolyl group, or a five membered heterocyclic ring being optionally substituted and being stable to a reduction reaction, wherein said quinolyl group or said isoquinolyl group may be partially or wholly hydrogenated, with the proviso that $R^{53}$ and $R^{63}$ do not combine with the adjacent nitrogen atom to form phtharazinyl, or a pharmaceutically acceptable salt thereof, which comprises subjecting a compound of the formula (VI):

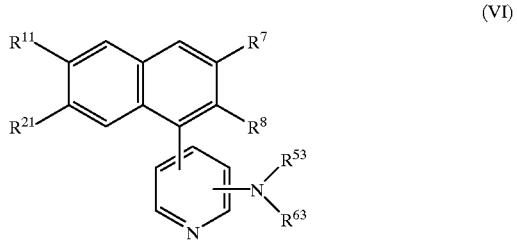

(VI)

wherein $R^{11}$ and $R^{21}$ are the same or different and are each a hydrogen atom or a protected or unprotected hydroxy group, either one of $R^7$ and $R^8$ is a free or esterified carboxyl group, and another one is a hydrogen atom, a lower alkyl group, or a free or esterified carboxyl group, and other symbols are the same as defined above, or an internal acid anhydride compound thereof to a reduction, and where $R^{11}$ and/or $R^{21}$ are a protected hydroxy group, optionally followed by removing protecting groups for the hydroxy groups, and if necessary, re-protecting the hydroxy group(s) at 6- and/or 7-positions or the hydroxymethyl moieties at 2- and/or 3-positions, and optionally, protecting whole hydroxy groups or hydroxymethyl moieties, and optionally, converting into a pharmaceutically acceptable salt thereof.

* * * * *

UNITED STATES PATENT AND TRADEMARK OFFICE
CERTIFICATE OF CORRECTION

PATENT NO.     : 6,214,996 B1
DATED          : April 10, 2001
INVENTOR(S)    : Tatsuzo Ukita et al.

It is certified that error appears in the above-identified patent and that said Letters Patent is hereby corrected as shown below:

<u>Title page,</u>
Item [54], Title, DERIVATES" should read -- DERIVATIVES --

<u>Column 93, claim 3,</u>
Line 48, "$R^1$" should read -- $R^6$ --.

Signed and Sealed this

Second Day of April, 2002

*Attest:*

JAMES E. ROGAN
*Attesting Officer*  *Director of the United States Patent and Trademark Office*

UNITED STATES PATENT AND TRADEMARK OFFICE
CERTIFICATE OF CORRECTION

PATENT NO.   : 6,214,996 B1
DATED        : April 10, 2001
INVENTOR(S)  : Tatsuzo Ukita et al.

It is certified that error appears in the above-identified patent and that said Letters Patent is hereby corrected as shown below:

<u>Column 95,</u>
Lines 23-24, "1-{2-4 pyridyl}-2,3-bis(hydroxymethyl)-6,7-dimethoxynaphthalene" should read -- 1-{2-[1(2H)-isoquinolinon-2-yl]-4-pyridyl}-2,3-bis(hydroxymethyl)-6-7-dimethoxynaphthalene --.

Signed and Sealed this

Eleventh Day of March, 2003

JAMES E. ROGAN
*Director of the United States Patent and Trademark Office*